(12) United States Patent
Fujita et al.

(10) Patent No.: US 8,440,426 B2
(45) Date of Patent: May 14, 2013

(54) METHOD FOR PRODUCTION OF ANTIMUTAGENIC SUBSTANCE USING LACTIC ACID BACTERIUM

(75) Inventors: Minoru Fujita, Nishitokyo (JP); Masaharu Nakayama, Hanishina-gun (JP); Yasuteru Nakamura, Hanishina-gun (JP); Takahiro Inoue, Bunkyo-ku (JP)

(73) Assignee: Kigen Biogenics Institute Co., Ltd., Chiyoda-ku, Tokyo (JP)

( * ) Notice: Subject to any disclaimer, the term of this patent is extended or adjusted under 35 U.S.C. 154(b) by 554 days.

(21) Appl. No.: 12/450,817

(22) PCT Filed: Apr. 18, 2008

(86) PCT No.: PCT/JP2008/057623
§ 371 (c)(1),
(2), (4) Date: Feb. 12, 2010

(87) PCT Pub. No.: WO2008/130036
PCT Pub. Date: Oct. 30, 2008

(65) Prior Publication Data
US 2010/0143965 A1  Jun. 10, 2010

(30) Foreign Application Priority Data
Apr. 18, 2007  (JP) .................... 2007109656

(51) Int. Cl.
*C12P 1/00* (2006.01)

(52) U.S. Cl.
USPC .......... 435/41; 435/170; 435/243; 435/252.1; 435/252.9

(58) Field of Classification Search .................. None
See application file for complete search history.

(56) References Cited

U.S. PATENT DOCUMENTS 5,354,687 A  10/1994  Hashimoto et al.
6,827,953 B1  12/2004  Mizutani et al.

FOREIGN PATENT DOCUMENTS

| JP | 8-056650 A | 3/1996 |
| JP | 10-276770 A | 10/1998 |
| JP | 2825761 B2 | 11/1998 |
| JP | 11-113564 A | 4/1999 |
| JP | 11-221071 A | 8/1999 |
| JP | 3209784 B2 | 9/2001 |
| JP | 2002171933 * | 6/2002 |
| JP | 2006-291146 A | 10/2006 |

OTHER PUBLICATIONS

Lankaputhra et al., Mutation Research, 1998, vol. 397, p. 169-182.*
Coconnier, M., et al., Antagonistic Activity against Helicobacter infection In Vitro and In Vivo by the Human *Lactobacillus acidophilus* Strain LB, Applied and Environmental Microbiology, vol. 64, No. 11, Nov. 1998, pp. 4573-4580.
Geier, M., et al., Probiotics, Prebiotics and Synbiotics: A Role for Prevention for Colorectal Cancer? Cancer Biology & Therapy, vol. 5, No. 10, Oct. 2006, pp. 1265-1269.
Hayakawa, K., et al., Effect of a Gamma-Aminobutyric Acid-Enriched Dairy Product on the Blood Pressure of Spontaneously Hypertensive and Normotensive Wistar-Kyoto Rats, British Journal of Nutrition, vol. 92, 2004, pp. 411-417.
Hosono, A., et al., Antimutagenic Properties of Lactic Acid-Cultured Milk on Chemical and Fecal Mutagens, Journal of Dairy Science, vol. 69, 1986, pp. 2237-2242.
Lin, D., et al., Probiotics as Functional Foods, Nutrition in Clinical Practice, vol. 18, Dec. 2003, pp. 497-506.
Ljungh, A., et al., Lactic Acid Bacteria as Probiotics, Current Issues in Intestinal Microbiology, vol. 7, 2006, pp. 73-89.
Park, H., et al., Antimutagenic Activity of *Lactobacillus plantarum* KLAB21 Isolated from kimchi Korean Fermented Vegetables, Biotechnology Letters, vol. 23, 2001, pp. 1583-1589.
Sashihara, T., et al., An Analysis of the Effectiveness of Heat-Killed Lactic Acid Bacteria in Alleviating Allergic Diseases, Journal of Dairy Science, vol. 89, 2006, pp. 2846-2855.
Wollowski, I., et al., Bacteria Used for the Production of Yogurt Inactivate Carcinogens and Prevent DNA Damage in the Colon of Rats, Journal of Nutrition, vol. 129, 1999, pp. 77-82.
Wollowski, I., et al., Protective Role of Probiotics and Prebiotics in Colon Cancer, American Journal of Clinical Nutrition, vol. 73 (Supplement), 2001, pp. 451S-455S.

* cited by examiner

*Primary Examiner* — Kade Ariani
(74) *Attorney, Agent, or Firm* — Chapman and Cutler LLP

(57) ABSTRACT

Disclosed is a method for producing an antimutagenic substance by using a lactic acid bacteria, which can produce the antimutagenic substance in a large quantity in an extremely simple manner and is economically advantageous; particularly a method for producing an antimutagenic substance effective for a carcinogenic substance, particularly a heterocyclic amine (HCA) which is a carcinogenic substance derived from a food, by using a lactic acid bacteria. Specifically disclosed is a method for producing an antimutagenic substance by using a lactic acid bacteria, which is characterized by suspending the lactic acid bacteria in a poorly nutrient or nutrient-free medium and leaving the lactic acid bacteria in the medium. Preferably, the poorly nutrient or nutrient-free medium is selected from the group consisting of physiological saline, a phosphate-buffered saline without a calcium or magnesium salt (PBS (−)), a citrate buffer, a distilled water, an ion-exchanged water, a natural water, a well water, a tap water, a mineral-added water, a vitamin-added water, an ion supply beverage for an athlete and the like. More preferably, the lactic acid bacteria is *Lactobacillus plantarum* strain KK-2503 or *Lactobacillus alimentarius* strain KN-15.

2 Claims, 11 Drawing Sheets

METHOD FOR PRODUCTION OF ANTIMUTAGENIC SUBSTANCE USING LACTIC ACID BACTERIUM

TECHNICAL FIELD

The present invention relates to a method for production of an antimutagenic substance using a lactic acid bacterium, and in particular, to a method for producing an antimutagenic substance by leaving lactic acid bacteria suspended in a nutrient-free (oligotrophic or atrophic) medium.

BACKGROUND ART

It is widely recognized that lactic acid bacteria generally have effects of calming intestinal disorders, and many food products, such as yoghurt, and medical products, such as medicine for intestinal disorders, are available on the market.

In particular, it has become clear in recent years that lactic acid bacteria have various functions in addition to the above described effects of calming intestinal disorders, for example probiotic functions, prebiotic functions and biogenic functions.

As concerns functions of lactic acid bacteria other than those of calming intestinal disorders, prevention of hypertension, as a result of production of GABA (Non-Patent Document 1), alleviation of allergy symptoms, as a result of improvement of the immune balance when bacterial cells are ingested (Non-Patent Document 2), and elimination of *Helicobacter pylori*, as a result of lactic acid, which is the main product (Non-Patent Document 3) have been discovered.

In addition, there are many reports that lactic acid bacteria also have effects of preventing cancer, and particularly their effects of preventing colon cancer have been verified in experiments using animals.

There are various theories concerning the mechanism behind the colon cancer preventing effects of lactic acid bacteria, and according to one hypothesis relating to so-called pathogenic bacteria and probiotic bacteria, for example, ingestion of products containing live lactic acid bacteria or lactic acid bacteria byproducts lowers the pH in the intestines, so that probiotic bacteria, such as bifidobacteria, from among bacteria that form bacterial flora within the intestines, proliferate and pathogenic bacteria, such as Welch *bacillus*, are eliminated, and as a result, the inside of the intestines improves, and the occurrence of colon cancer is reduced.

According to another hypothesis, intercellular components, such as nucleic acid, bacterial wall components, such as muramyl dipeptide, and components of lactic acid bacterial bodies, such as extracellular polysaccharides, activate the immune system of the intestinal mucosa through various TLR's (toll-like receptors), and as a result, microscopic cancer cells in their initial stage are eliminated by active microphages and the like, which helps prevent colon cancer.

Furthermore, according to another hypothesis, ingested lactic acid bacteria adsorb carcinogenic substances, such as nitrosamine, which is generated as a putrefactive product within the intestine, and mutagenic substances originating from food on the surface of bacteria, so that they are discharged from the body together with the feces, and as a result, colon cancer can be prevented. According to this hypothesis, some strains of lactic acid bacteria have strong antimutagenic properties due to the effects of mutagens adsorbed in the bacterial body. Some of these are disclosed in patent gazettes (Patent Documents 1, 2, 3, 4 and 5).

In addition to the above, there is hypothesis according to which lactic acid bacteria generate anticarcinogenic substances and thus more directly prevent colon cancer, and there are reports of a phenomenon, which hints at the existence of such a substance as a result of study of yoghurt, for example. However, none of them have been corroborated, and no substance that prevents colon cancer can be specified.

There are many other hypotheses, and it can be assumed that all of these mechanisms assumed to prevent colon cancer relate to each other in varying degrees (Non-Patent Documents 4, 5, 6, 7, 8, 9 and 10).

As described above, the lactic acid bacterial components active in the prevention of colon cancer and the mechanism are not yet clearly understood, and, of course, there is no decisive proof that lactic acid bacteria have or produce antimutagenic substances. Furthermore, an effective method for producing or extracting antimutagenic substances from lactic acid bacteria has yet to be proposed.

Non-Patent Document 1: Hayakawa K. et al. Effect of a gamma-aminobutyric acid-enriched dairy product on the blood pressure of spontaneous hypertensive and normotensive Wistar-Kyoto rats. Br. J. Nutr. 2004, 92. 411-417.

Non-Patent Document. 2: Sashihara T. et al. An analysis of the effectiveness of heat-killed lactic acid bacteria in alleviating allergic diseases. J. Dairy Sci. 2006, 89. 2846-2855.

Non-Patent Document 3: Coconnier M. H. et al. Antagonistic activity against *Helicobacter* infection in vitro and in vivo by the human *Lactobacillus acidophilus* strain LB. Appl. Environ. Microviol. 1998, 64. 4573-4580.

Non-Patent Document 4: Lin D C. Probiotics as functional foods. Nutr. Clin. Pract. 2003, 18. 497-506.

Non-Patent Document 5: Ljungh A. and Wadstrom T. Lactic acid bacteria as probiotics. Curr. Issues Intest. Microbiol. 2006, 7. 73-89.

Non-Patent Document 6: Geier M S. et al. Probiotics, prebiotics and synbiotics: a role in chemo prevention for colorectal cancer? 2006, 5. 1265-1269.

Non-Patent Document 7: Hosono A. and Kashina T. Antimutagenic properties of Lactic acid-cultured milk on chemical and fecal mutagens. J. Dairy Sci. 1986, 69. 2237-2242.

Non-Patent Document 8: Sudarshan R. et. al. Effects of hydrolysis of milk glycerides on the antimutagenicity of a hexane extract of milk. J. Dairy Sci. 1998, 81. 664-671.

Non-Patent Document 9: Wollowski I. et al. Bacteria used for the production of yoghurt inactivate carcinogens and prevent DNA damage in the colon of rats. J. Nutr. 1999, 129. 77-82.

Non-Patent Document 10: Wollowski I. et al. Protective role of probiotics and prebiotics in colon cancer. Am. J. Clin. Nutr. 2001, 73. 4515-455S.

Patent Document 1: Japanese Patent No. 3209784
Patent Document 2: Japanese Patent No. 2825761
Patent Document 3: Japanese Unexamined Patent Publication H08 (1996)-056650
Patent Document 4: Japanese Unexamined Patent Publication H10 (1998)-276770
Patent Document 5: Japanese Unexamined Patent Publication H11 (1999)-113564

DISCLOSURE OF THE INVENTION

Problem to Be Solved by the Invention

The biggest problem with administering lactic acid bacteria in order to gain effects of preventing cancer is that most of the administered lactic acid bacteria die in the stomach and intestines, and in order to prevent the death of lactic acid bacteria, it is necessary to carry out a great number of tests for screening strains of lactic acid bacteria so that bacterial strains having resistance to gastric acid, intestinal fluid, gall and the like can be selected, to prepare lactic acid bacteria having resistance to digestive fluids using a technique for genetic recombination, or to administer lactic acid bacteria in the form of enteric coated capsules.

It is uncertain whether or not the bacteria will settle, even when selected to have resistance to digestive liquids, and almost no lactic acid bacteria sold as probiotic products settle for a long period of time, even if they can stay in the stomach and colon for a short period of time. Accordingly, in the case where prevention of cancer is attempted by ingesting such live bacteria, it is necessary to keep ingesting a considerable amount of live bacteria every day. In addition, lactic acid bacteria settle only for a short period of time, and therefore, it is unclear whether or not they have sufficient metabolic activity at the point where they settle.

In addition, bacterial cells, or bacterial cell fragments, of new strains of lactic acid bacteria having conventional antimutagenic properties are said to have antimutagenic properties, but these lactic acid bacteria do not produce antimutagenic substances. Most conventional strains of lactic acid bacteria having antimutagenic properties have effects of adsorbing mutagens on the bacterial cells according to the mechanism behind their effects, and therefore, it is necessary to ingest bacterial cells or bacterial cell fragments in order to use lactic acid bacteria.

As for substances referred to as lactic acid bacteria byproducts and supernatant fluids in the culture of lactic acid bacteria, it is unclear whether there are substances effective for preventing cancer in these, even at the test tube stage. According to most explanations concerning the mechanism behind their effects, some substances produced by lactic acid bacteria aid proliferation of probiotic bacteria, such as bifidobacteria, which leads to improvement of the inside of the intestines and indirectly prevents cancer. However, this hypothesis is yet to be proven, as described above.

Though attempts have been made to detect antimutagenic substances in culture liquids for lactic acid bacteria, including yoghurt so that the substance could be mass produced, this has not yet been achieved. It is clear that the biggest reason for this lies in the highly complex composition of culture liquids for lactic acid bacteria. In particular, various organic acids produced by lactic acid bacteria and various amino acids in the composition of culture media greatly affect testing methods of various types for detecting antimutagenic properties, such as the Ames test. Though in order to eliminate these, ultrafiltration, dialysis membrane methods, gel filtration methods and various chromatographic column methods can be used, in many cases they result in elimination of the antimutagenic substance as well, or conversely, in many cases antimutagenic substance originating from the culture media will be detected, making for false positive results. At the same time, there is a lot of cost and effort involved in the method for eliminating foreign substances.

Accordingly, an object of the present invention is to solve the above described problems and provide an extremely easy mass production method which is economically advantageous, according to which a large amount of water soluble antimutagenic substances which are effective against various carcinogenic substances can be produced from lactic acid bacteria cells.

In particular, the invention provides a method for producing an antimutagenic substance originating from lactic acid bacteria which is effective against heterocyclic amine (HCA), which is a carcinogenic substance originating from food having extremely strong carcinogenic properties, even in small amounts, which is included in great amounts in burnt meat and fish.

Means for Solving Problem

The present inventors found as a result of diligent research that lactic acid bacteria posess antimutagenic substances which are effective against carcinogenic substances, particularly heterocyclic amine (HCA), which is a carcinogenic substance originating from food, and antioxidants which work against active oxygen species in the suspension medium when live lactic acid bacterial cells are suspended in an oligotrophic or atrophic medium, such as physiological saline, phosphate buffered saline (PBS), citrate buffered solutions, distilled water or ion exchange water, unlike conventional culture media for bacteria, and it is processed for a medium to long period of time at a middle to low temperature or for a short period of time at a high temperature, for example in a boiling process, and then arrived at the present invention.

Furthermore, they found that antimutagenic substances which are effective against HCA and antioxidants which work against active oxygen species are instantly generated in the suspension medium at room temperature when live lactic acid bacteria are once dried using a method from among a freeze drying method, a heat drying method, a reduced pressure drying method and a spray drying method, and suspended in the above described medium. They also found that the above described heat drying method and reduced pressure drying method do not at all affect the generation of antimutagenic substances, though the bacteria die out during heating.

They also found that some bacterial strains may instantly generate antimutagenic substances in a solution, depending on the salt concentration, simply when suspended in certain types of salt solutions, even in the case where the live lactic acid bacteria are not dried.

Here, the above described activity can be gained in suspension solutions simply by physically crushing lactic acid bacterial cells in accordance with such a method as ultrasound process, an enzyme process or crushing using beads or pressing, which are conventional methods, and after that suspending the crushed fragments in distilled water or the like.

That is to say, the method for production of antimutagenic substance using a lactic acid bacterium according to claim 1 is a method characterized in that lactic acid bacteria are left suspended in an oligotrophic medium or in an atrophic medium.

In addition, the method for production of antimutagenic substance using a lactic acid bacterium according to claim 2 is a method for production of antimutagenic substance using a lactic acid bacterium according to claim 1, characterized in that the oligotrophic medium or atrophic medium is selected from the group consisting of calcium salt and magnesium salt-free phosphate buffered saline (PBS(−)), calcium salt and magnesium salt-added phosphate buffered saline (PBS(+)), phosphate buffered liquids, $KH_2PO_4$/NaOH buffered liquids, Tris/HCl buffered liquids, citric acid buffered liquids, citric acid/NaOH buffered liquids, citric acid/sodium citrate buffered liquids, HEPES buffered liquids, sodium borate/HCl buffered liquids, boric acid/NaOH buffered liquids, sodium borate/NaOH buffered liquids, sodium carbonate/sodium hydrogen carbonate buffered liquids, sodium hydrogen carbonate/NaOH buffered liquids, NaH maleate/NaOH buffered liquids, maleic acid/Tris/NaOH buffered liquids, KH phthalate/NaOH buffered liquids, sodium cacodylate/HCl buffered liquids, acidic acid/sodium acetate buffered liquids, acidic acid/NaOH buffered liquids, succinic acid/NaOH buffered liquids, tartaric acid/NaOH buffered liquids, imidazole/HCl buffered liquids, vicine/NaOH buffered liquids, glycine/NaOH buffered liquids, $Na_2HPO_4$/NaOH buffered liquids, NaOH/KCl buffered liquids, lithium salt liquids, sodium liquids, potassium liquids, magnesium salt liquids, calcium salt liquids, diluted hydrochloric acid, diluted sulfuric acid, ion-exchanged water, distilled water, pure water, ultrapure water, natural water, well water, tap water, mineral-added water, vitamin-added water, and sports drinks.

Furthermore, the method for production of antimutagenic substance using a lactic acid bacterium according to claim 3 is a method for production of antimutagenic substance using a lactic acid bacterium according to claim 1 or 2, characterized in that the lactic acid bacteria are *Lactobacillus plantarum* KK-2503 strains or *Lactobacillus alimentarius* KN-15 strains.

Preferably, the method for production of antimutagenic substance using a lactic acid bacterium according to claim 4 is a method for production of antimutagenic substance using a lactic acid bacterium according to claim 3, characterized in that the antimutagenic substance is an antimutagenic substance acting against heterocyclic amines.

Here, in the present specification, antimutagenic substances generated in accordance with the above described method are referred to as "antimutagenic substances of lactic acid bacteria" and sometimes abbreviated to "AMS-LAB."

EFFECTS OF THE INVENTION

In accordance with the method for production of an antimutagenic substance using a lactic acid bacterium according to the present invention, live lactic acid bacterial cells are suspended in an oligotrophic or atrophic medium and left for a medium to long period of time at a middle or low temperature or for a short period of time at a high temperature, or live lactic acid bacteria are once dried using a method from among a freeze drying method, a heat drying method, a reduced pressure drying method or a spray drying method, and suspended in a medium as that described above, or depending on the bacterial strain, wet bacteria may simply be suspended in a certain type of salt solution without being dried, and thus, a large amount of antimutagenic substance that is effective against various types of carcinogenic substances, particularly HCA, which is a carcinogenic substance originating from food, can be generated in the suspension liquid in accordance with an extremely simple method. Accordingly, an inexpensive, economic antimutagenic substance can be mass produced.

Furthermore, there are fractions having antioxidant performance in AMS-LAB, and therefore, they can be expected to have antioxiclizing effects.

BRIEF DESCRIPTION OF THE DRAWINGS

FIG. 1-2 is a graph showing the relationship between the temperature at which KK-2503 is left suspended in PBS(−) liquid and the antimutagenic activity against HCA;

FIG. 2-1 is a graph showing the relationship between the temperatures at which KN-15 is left suspended in PBS(−) liquid, 50° C. and 98° C., and the antimutagenic activity against HCA;

FIG. 2-2 is a graph showing the relationship between the temperatures at which KK-2503 is left suspended in PBS(−) liquid, 50° C. and 98° C., and the antimutagenic activity against HCA;

FIG. 3-1 is a graph showing the relationship between KN-15 suspended in various types of buffered liquids and the antimutagenic activity against HCA;

FIG. 3-2 is a graph showing the relationship between KK-2503 suspended in various types of buffered liquids and the antimutagenic activity against HCA;

FIG. 4-1 is a graph showing the relationship between the bacterial cells of KN-15 dried in accordance with various methods and suspended in a PBS(−) liquid, and the antimutagenic activity against HCA;

FIG. 4-2 is a graph showing the relationship between the bacterial cells of KK-2503 dried in accordance with various methods and suspended in a PBS(−) liquid, and the antimutagenic activity against HCA;

FIG. 5-1 is a graph showing the relationship between the dried and wet bacterial cells of KN-15 suspended in a PBS(−) liquid and in distilled water, and the antimutagenic activity against HCA;

FIG. 5-2 is a graph showing the relationship between the dried and wet bacterial cells of K-2503 suspended in a PBS(−) liquid and in distilled water, and the antimutagenic activity against HCA;

FIG. 6-1 is a graph showing the relationship between the dried bacterial cells of KN-15 suspended in saline with various concentrations and the antimutagenic activity against HCA;

FIG. 6-2 is a graph showing the relationship between the dried bacterial cells of KK-2503 suspended in saline with various concentrations and the antimutagenic activity against HCA;

FIG. 7-1 is a graph showing the degree of resistance of KN-15 to the digestive liquid of AMS-LAB/PBS(−);

FIG. 7-2 is a graph showing the degree of resistance of KK-2503 to the digestive liquid of AMS-LAB/PBS(−);

FIG. 8-1 is a graph showing by means of a comet assay the results of defense action of the product gained by freeze drying AMS-LAB of KN-15 against the liver cell nuclei in a CD1 mouse administered with DMH;

FIG. 8-2 is a graph showing by means of a comet assay the results of defense action of the product gained by freeze drying AMS-LAB of KN-15 against the colon mucous membrane cell nuclei in a CD1 mouse administered with DMH;

FIG. 9-1 is a graph showing the relationship between the lactic acid standard strain and the antimutagenic activity against HCA when live bacteria is left for 30 minutes at 50° C. after being suspended in PBS(−);

FIG. 9-2 is a graph showing the relationship between standard strains of lactic acid and the antimutagenic activity against HCA when live bacteria is freeze dried, and then, stirred and suspended in 0.8 mass % of saline.

BEST MODE FOR CARRYING OUT THE INVENTION

Figure 1:
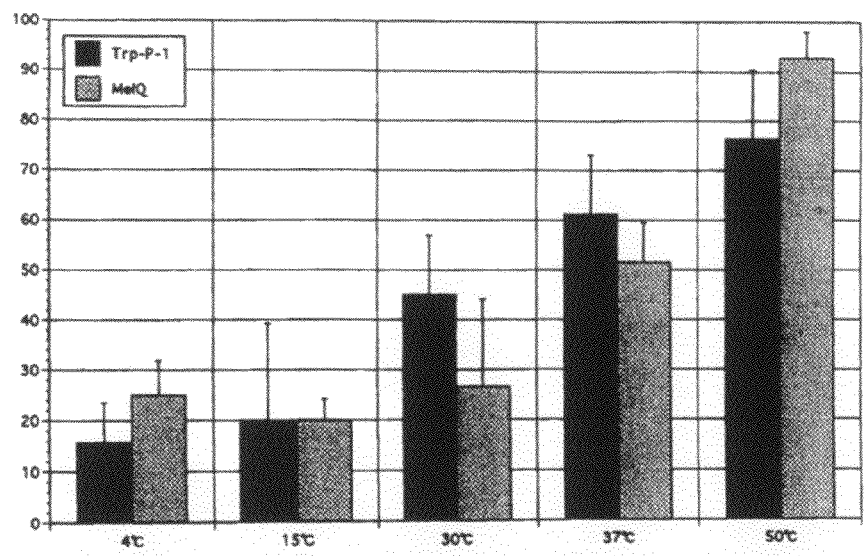
FIG. 1-1 is a graph showing the relationship between the temperature at which KN-15 is left suspended in PBS(−) liquid and the antimutagenic activity against HCA.

One of the methods for production of an antimutagenic substance using a lactic acid bacterium according to the present invention is a method for leaving lactic acid bacteria suspended in an oligotrophic or atrophic medium.

That is to say, antimutagenic substances (AMS-LAB) can be easily generated by leaving lactic acid bacteria in an oligotrophic or atrophic state at a high temperature or a low temperature.

Another method for production of an antimutagenic substance using a lactic acid bacterium according to the present invention is a method for suspending lactic acid bacteria in an oligotrophic or atrophic medium after drying the lactic acid bacteria. That is to say, bacterial cells can be dried in accordance with any method and suspended in the above described medium so that AMS-LAB is instantly generated in the suspension liquid.

First, lactic acid bacteria which can be used in the method for production of an antimutagenic substance using a lactic acid bacterium according to the present invention are described.

Though the lactic acid bacteria that can be used in the present invention are not particularly limited and any available lactic acid bacteria can be used, *Lactobacillus plantarum* and *Lactobacillus alimentarius* lactic acid bacteria are preferable, and *Lactobacillus plantarum* KK-2503 (hereinafter referred to as "KK-2503") and *Lactobacillus alimentarius* KN-15 (hereinafter referred to as "KN-15") are more preferable for use.

These lactic acid bacteria KK-2503 and KN-15 are strains of lactic acid bacteria extracted from Japanese pickles, which are a traditional fermented food, by the present inventors, and deposited in the Incorporated Administrative Agency National Institute of Technology and Evaluation Patent Microorganisms Depositary (NPMD) (2-5-8 Kazusakamatari Kisarazu-shi, Chiba-ken 292-0818, JAPAN), which is an international depositary authority under the Budapest treaty on the international recognition of the deposit of microorganisms. The details of the certificates for acceptance of deposition and existence are as follows.

(1) *Lactobacillus plantarum* KK-2503

Accession number: NITE BP-334

Accession date: Mar. 13, 2007

Accession: The microscopic organisms in column I of accession number NITE AP-334 received on Mar. 13, 2007, original day of deposition) were accepted (*Lactobacillus plantarum* KK-2503, accession number NITE P-334).

Receipt of claim of transfer: The claim of transfer from the deposition of NITE P-334 on March 13 (date of original deposition) in 2007 to deposition under the Budapest treaty was received on Mar. 4, 2008 (date of transfer).

Results of existence test: The above international depositary authority conducted an existence test on Mar. 7, 2008 in order to confirm the existence of the microorganisms.

(2) *Lactobacillus alimentarius* KN-15

Accession number: NITE BP-333

Accession date: Mar. 13, 2007

Accession: The microscopic organisms in column I of accession number NITE AP-333 received on Mar. 13, 2007, original day of deposition) were accepted (Lactobacillus alimentarius KN-15, accession number NITE P-333).

Receipt of claim of transfer: The claim of transfer from the deposition of NITE P-333 on March 13 (date of original deposition) in 2007 to deposition under the Budapest treaty was received on Mar. 4, 2008 (date of transfer).

Results of existence test: The above international depositary authority conducted an existence test on Mar. 7, 2008 in order to confirm the existence of the microorganisms.

These two bacterial strains KK-2503 and KN-15 that are preferable for use are bacterial strains having particularly high antimutagenic activity and selected from among 121 strains of lactic acid bacteria which were extracted from commercially available pickles and identified by the present inventors after the below described Ames test, and are particularly effective for use in the present invention.

The method for extracting *Lactobacillus plantarum* KK-2503 (accession number NITE BP-334) and *Lactobacillus alimentarius* KN-15 (accession number NITE BP-333) is as follows.

<Method for Extracting KK-2503>

KK-2503 was extracted basically in accordance with the method in Okada et al. (Science and Technology and Lactic Acid Bacteria: Academic Society Publishing Center).

Concretely, an appropriate amount of rice bran was taken from a rice bran bed for pickles and diluted to 1/10 of its original concentration with sterilized PBS (−), and a culture medium of GYP white agar (having the same composition as in the above document) was inoculated with 100 µl of this, and the result was cultured aerobically at 30° C. for 48 hours. Bacteria were picked out from colonies with the appearance of transparent ring in the culture medium as an indicator, and the same culture medium was further inoculated with this, so that a single colony formed. This operation was repeated, and after that bacteria were picked out from the gained single colony, and an MRS liquid culture medium was inoculated with these and cultured at 30° C. for 24 hours. This was centrifugally separated at 1500 G for 20 minutes so that the bacterial cells could be collected and condensed to twice their original concentration, and floated in a fresh, sterilized MRS liquid culture medium with 10% of DMSO added. This was put in a 1 ml sterilized vial and frozen and preserved at −80° C.

This was unfrozen before use.

<Means for Extracting KK-15>

KK-15 was extracted basically in accordance with the method in Okada et al. (Science and Technology and Lactic Acid Bacteria: Japan Scientific Societies Press).

Concretely, a commercially available cucumber pickled in rice bran was homogenized and diluted to 1/10 of its original concentration with sterilized PBS (−), and a culture medium of GYP white agar (having the same composition as in the above document) was inoculated with 100 µl of this, and the result was cultured aerobically at 30° C. for 48 hours. Bacteria were picked out from colonies with the appearance of transparent ring in the culture medium as an indicator, and the same culture medium was further inoculated with this, so that a single colony formed. This operation was repeated, and after that bacteria were picked out from the gained single colony, and an MRS liquid culture medium was inoculated with these and cultured at 30° C. for 24 hours. This was centrifugally separated at 1500 G for 20 minutes so that the bacterial cells could be collected and condensed to twice their original concentration, and floated in a fresh, sterilized MRS liquid culture medium with 10% of DMSO added. This was put in a 1 ml sterilized vial and frozen and preserved at -80° C.

This was unfrozen before use.

In addition, Table 1 shows the bacterial properties of the KK-2503 bacterial strain and Table 2 shows the bacterial properties of the KN-15 bacterial strain.

TABLE 1 a) separation source: rice bran bed
b) colony type on GYP medium: white circular colony with transparent ring
c) morphological properties
　(1) type: Gram positive bacteria

TABLE 1-continued d) physiological properties
  (1) Gram staining: +   (2) spores: –
  (3) mobility: –         (4) reaction to oxygen: anaerobic
  (5) catalase: –         (6) generation of gas from glucose: –
e) fermentative properties of sugar (AP150CH: bioMérieux Japan Ltd.)
  glycerol: –
  erythritol: –
  D arabinose: –
  L arabinose: +
  ribose: +
  D xylose: –
  L xylose: –
  adonitol:
  beta-methyl-D-xyloside: –
  galactose: +
  glucose: +
  fructose: +
  mannose: +
  sorbose: –
  rhamnose: +
  dulcitol: –
  inositol: –
  mannitol: +
  sorbitol: +
  alpha-methyl-D-mannoside: –
  alpha-methyl-D-glucoside: +
  N acetyl glucosamine: +
  amygdaline: +
  arbutin: +
  esculine: +
  salicin: +
  cellobiose: +
  maltose: +
  lactose: +
  melibiose: +
  sucrose: +
  trehalose: +
  inulin: –
  melezitose: –
  raffinose: +
  starch: –
  glycogen: –
  xylitol: –
  gentiobiose: +
  D turanose: +
  D lyxose: –
  D tagatose: –
  D fucose: –
  L fucose: –
  D arabitol: –
  L arabitol: –
  gluconate: +
  2 ketogluconate: –
  5 ketogluconate: –

TABLE 2 a) morphological properties
  (1) type: bacteria
b) physiological properties
  (1) Gram staining: +   (2) spores: –
  (3) mobility: –         (4) reaction to oxygen: anaerobic
  (5) catalase: –         (6) generated lactic acid: DL
  (7) generation of gas from glucose: –
c) fermentative properties of sugar (AP150CH: bioMérieux Japan Ltd.)
  glycerol: –
  erythritol: –
  D arabinose: –
  L arabinose: –
  ribose: +
  D xylose: +
  L xylose: –
  adonitol: –
  beta-methyl-D-xyloside: –
  galactose: –
  glucose: +
  fructose: +

TABLE 2-continued mannose: +
  sorbose: –
  rhamnose: –
  dulcitol: –
  inositol: –
  mannitol: –
  sorbitol: –
  alpha-methyl-D-mannoside: –
  alpha-methyl-D-glucoside: +
  N acetyl glucosamine: +
  amygdaline: +
  arbutin: +
  esculine: +
  salicin: +
  cellobiose: +
  maltose: +
  lactose: –
  melibiose: +
  sucrose: +
  trehalose: +
  inulin: –
  melezitose: –
  raffinose: +
  starch: –
  glycogen: –
  xylitol: –
  gentiobiose: +
  D turanose: +
  D lyxose: –
  D tagatose: –
  D fucose: –
  L fucose: –
  D arabitol: –
  L arabitol: –
  gluconate: +
  2 ketogluconate: –
  5 ketogluconate: –

Judging from the above properties, the lactic acid bacteria KK-2503 can be considered to be bacteria belonging to the *lactobacillus* genus. When identified using API LAB software (bioMerieux Japan Ltd.), which is a bacteria type identifying database on the basis of the results of the fermentative properties of sugar, the probability of the lactic acid bacteria being *Lactobacillus plantarum* was 82.6° A, and the probability of them being *Lactobacillus pentosus* was 17.3%. When the base sequence of the 16 S ribosome RNA of this microorganism was further analyzed (international base sequence database (GenBank/DDBJ/EMBL)), the homogeny was strong only between the *Lactobacillus plantarum* and the *Lactobacillus pentosus* (99.9%).

Judging from the above comprehensive results, the lactic acid bacteria KK-2503 can be considered to be microorganisms belonging to the *Lactobacillus plantarum* species, which is entrusted with the Independent Administrative Institute Product, Evaluating Technology Base Mechanism Patent Microorganism Deposition Center with the accession number NITE BP-334, as described above.

In addition, judging from the above properties, the lactic acid bacterium KN-15 can be considered to belong to the *Lactobacillus* genus, and when the 500 base sequence of the 16 S ribosome RNA of this microorganism was analyzed (international base sequence database (GenBank/DDBJ/EMBL)), the homogeny was strong with *Lactobacillus alimentarius* (98.5%), and furthermore, a molecular phylogenic tree was prepared in accordance with a neighbor combining method, and as a result, a cluster of only *Lactobacillus alimentarius* was formed. Accordingly, the lactic acid bacterium KN-15 can be considered to be a microorganism belonging to the *Lactobacillus alimentarius* species, which is entrusted with the Independent Administrative Institute Product Evaluating Technology Base Mechanism Patent Microorganism Deposition Center with the accession number NITE BP-333, as described above.

Next, the oligotrophic medium and atrophic medium that can be used in the method according to the present invention are described.

In the method according to the present invention, it is necessary to suspend lactic acid bacteria in an oligotrophic medium or an atrophic medium, such as the below described PBS (−) or distilled water in order to mass produce AMS-LAB. Though the lactic acid bacteria culture medium can be used as it is, in this ease, it becomes extremely difficult to detect and sample the substance because there are too many impurities, as described above. Accordingly, it is desirable to use a basic medium, such as distilled water or ion exchanged water, and for an appropriate amount of a certain type of salt, specifically a cation substance, such as sodium salt or magnesium salt, to be included.

Though any suspension medium can be used in the present invention, as long as the above described conditions can be satisfied, a suspension medium that can be eaten as it is and is safe to the human body is desirable, taking the following process into consideration. Furthermore, it is desirable for a certain amount of sodium, which is one of the components of cooking salt, and cations, such as potassium or magnesium, which are contained in food in large amounts, to be included. However, there are many strains of lactic acid bacteria that are active when suspended in distilled water and heated, and there are also strains of lactic acid bacteria that are active only when suspended in distilled water after being dried, even without being heated, and therefore, it is not necessary for ions to be included.

Examples of the suspension medium that can be used in the present invention are PBS(−), PBS(+), phosphate buffered liquids, $KH_2PO_4$/NaOH buffered liquids, Tris/HCl buffered liquids, citric acid/NaOH buffered liquids, citric acid/sodium citrate buffered liquids, HEPES buffered liquids, sodium borate/HCl buffered liquids, boric acid/NaOH buffered liquids, sodium borate/NaOH buffered liquids, sodium carbonate/sodium hydrogen carbonate buffered liquids, sodium hydrogen carbonate/NaOH buffered liquids, NaH maleate/NaOH buffered liquids, maleic acid/Tris/NaOH buffered liquids, KH phthalate/NaOH buffered liquids, sodium cacodylate/HCl buffered liquids, acidic acid/sodium acetate buffered liquids, acidic acid/NaOH buffered liquids, succinic acid/NaOH buffered liquids, tartaric acid/NaOH buffered liquids, imidazole/HCl buffered liquids, vicine/NaOH buffered liquids, glycine/NaOH buffered liquids, $Na_2HPO_4$/NaOH buffered liquids, NaOH/KCl buffered liquids, lithium salt liquids, sodium liquids, potassium liquids, magnesium salt liquids, calcium salt liquids, salt water of various concentrations, diluted hydrochloric acid, diluted sulfuric acid, ion-exchanged water, distilled water, pure water, ultrapure water, tap water, well water, natural water and the like, and the live lactic acid bacterial cells may be suspended in any medium that is safe for ingestion by humans, so that they can be used for health purposes.

That is to say, the type of medium is not necessarily limited to those listed above, and a water solution having an appropriate concentration of various inorganic substances, for example iron or various types of vitamins, such as vitamin C and vitamin B complexes, can be used. Furthermore, it is also possible to use these with an appropriate concentration of sweeteners. Accordingly, it is possible to use various types of sports drinks, where an appropriate vitamins and sweeteners are added to various inorganic ions in an appropriate concentration, as described above, as a suspension medium.

As described below, it is necessary to take the salt content and pH of the suspension medium into consideration when a test, such as an Ames test, follows, in the case of a buffered liquid.

In addition, vitamin C and calcium strongly affect the Ames test, and therefore, it is necessary to take the effects of additives into consideration when a test follows. Furthermore, the compatibility between the above described various types of suspension media and the used strains of lactic acid bacteria needs to be taken into consideration, and a test for appropriateness should be carried out whenever necessary.

Next, the Ames test, which is one test for confirming the above described antimutagenic properties, is described.

In the Ames test, *Salmonella typhimurium* TA 98 or the like that has lost its ability to synthesize histidine is put in contact with a carcinogenic substance, so that mutation of the *Salmonella typhimurium* accelerates, and a colony of the bacteria that has regained its ability to synthesize histidine through mutation is detected on a minimum glucose agar medium, and thus, the existence and degree of carcinogenic substances can be determined.

In the following, the concrete testing procedure for the Ames test on the above described *Lactobacillus plantarum* KK-2503 (KK-2503) and *Lactobacillus alimentarius* KN-15 (KN-15), which are appropriate strains of lactic acid bacteria is described in detail.

Reagent

Two reagents HCA: 3-amino-1,4-dimethyl-5H-pyrido[4,3-b]indole (Trp-P-1, made by Wako Pure Chemical Industries, Ltd.) and 2-amino-3,4-dimethylimidazo[4,5-f]quinoline (MeIQ, made by Wako Pure Chemical Industries, Ltd.), for example, are used, and an appropriate amount of HCA is dissolved in DMSO (dimethyl sulfoxide made by SIGMA Corporation) in advance, and after that, the whole is cryogenically preserved at −80° C. and defrosted when used while Trp-P-1 is distilled to 60 µM with sterilized distilled water and MeIQ is diluted to 1 µM for use.

SAMPLE

Lactic acid bacteria, such as KK-2503 and KN-15, are cultured in a medium which is appropriate for lactic acid bacteria to grow and proliferate, such as an MRS medium at 30° C., for example, but the medium is not limited to an MRS medium, and any medium can be used, as long as lactic acid bacteria can proliferate well. In addition, the temperature for culturing the bacteria is different depending on the type and strain of bacteria, and an appropriate temperature must be selected.

Culturing is stopped at the stage where the resting phase starts, after the logarithmic growth phase. In the case where bacteria which are still in the logarithmic growth phase or bacteria in the diminishing phase a long time after the resting phase are used, there is sometimes decrease in the activity and yield. This varies depending on the medium, the scale thereof, the amount of inoculation, the temperature for culturing and the like, and therefore, it is desirable to determine appropriate conditions through testing whenever necessary.

Live bacterial cells of each of the two strains of lactic acid bacteria (KK-2503 and KN-15) prepared in the above are centrifugally washed two times with sterilized distilled water. It is desirable to use distilled water cooled to approximately 4° C. to 10° C., and to centrifugally wash the cells at approximately 4° C. to 10° C. The gravity for centrifugal washing may be approximately 1000 G to 10,000 G, and it is desirable for it to be 7000 G or more, so that washing can be completed in a short period of time (10 minutes or less) if possible. In the case where the cells are centrifugally washed at approximately 1000 G to 1500 G, it is preferable for the temperature to be as low as 4° C. to 10° C., so that high activity can be maintained and the yield can be prevented from lowering.

In addition, it is desirable to use a cooled medium, as described above, in the case where centrifugal washing is carried out, and it should be noted that the activity and yield may lower in the case where centrifugal washing is carried out for a long period of time or at a high temperature.

The samples KK-2503 and KN-15 are respectively suspended in sterilized PBS (−), sterilized physiological saline or sterilized distilled water, which is equivalent to the culture after the above described centrifugal washing, and these were left still at an appropriate temperature. After that, the suspension liquid is centrifugally separated under the above described conditions for centrifugal separation, so that a supernatant can be adopted and filtered through a filter of approximately 0.2 μm for use (Sample 1 (KK-2503, KN-15)).

Other samples KK-2503 and KKN-15 are respectively centrifugally washed as described above and then dried, and after that suspended in sterilized PBS (−), sterilized physiological saline or sterilized distilled water, which is equivalent to the medium. In this case, the drying method may be any of a freeze drying method, a heat drying method, a reduced pressure drying method or a spray drying method. Two other samples of lactic acid bacteria (KK-2503 and KN-15) preserved at −80° C., as described above, are defrosted, and 10 ml of an MRS liquid culture medium (DIFCO Laboratories Inc.) is inoculated with 20 μl of the samples and cultured for 24 hours at 30° C. Next, this is transplanted once to the same medium and cultured for the same length of time at the same temperature, and after that centrifugally washed, and thus, live bacteria are gained. The gained live bacteria are once dried in accordance with a freeze drying method, a heat drying method, a reduced pressure drying method or a spray drying method, and suspended in an equal amount of oligotrophic medium or atrophic medium, such as PBS (−), as the original MRS liquid culture medium, and the thus gained suspension liquid is stirred for approximately 30 seconds with a vortex. Furthermore, bacterial cells are removed through centrifugal separation and the resulting supernatant is filtered with a filter of 0.2 μm and used as a sample (Sample 2 (KK-2503, KN-15)).

*Salmonella typhimurium*

*Salmonella typhimurium* TA 98 is gained from the Institute for Fermentation, and a bacterial strain preserved at −80° C. is defrosted, and then 50 ml of a nutrient broth (DIFCO Laboratories Inc.) with 0.5 mass % of NaCl is inoculated with 100 μl of the bacteria, and this is cultured for 12 hours at 37° C.: with a vibration of 120 times/min. This was used as a sample.

S-9 Mixture

A S-9 for Ames Test/Cofactor A kit is purchased from Oriental Yeast Co., Ltd. and used as a sample.

The method for manufacturing top agar, a minimum glucose agar culture medium, and a histidine and biotin solution is in compliance with the method for Ames testing or the like (Maron D. M. and Ames B. N. Revised methods for *Salmonella* mutagenicity test. Mutation Res. 1983, 113. 173-215).

In the following, the procedure is described in detail. A plastic test tube is put in an ice box and 200 μl of each of HCA, the sample and an S-9 mixture is put in this, and after that, reaction is induced at 37° C. with a revolution of 120 times/min. After 25 minutes of reaction, the test tube is again put in the ice box so that the reaction stops. 200 μl of the above described *salmonella* bacteria liquid kept at 10° C. after the completion of culturing and 4 ml of the above described top agar with histidine and biotin kept at 45° C. are added to the reacted liquid, which is then stirred, and after that, each sheet of the above described minimum glucose agar culture medium is inoculated with two ml of the reacted liquid. Two sheets of the minimum glucose agar culture medium are used for each sample.

This is cultured for 48 hours within an incubator at 37° C. and the number of colonies of the generated back mutation of the *Salmonella* bacteria is counted (hereinafter referred to as "back mutation colony number").

Test sections in which PBS (−) is added as a positive control instead of the above described sample and PBS (−) and distilled water are added as a negative control instead of the above described sample and HCA are provided, and the antimutagenic activity is represented as the rejection (%) in the test section for the samples against the positive control.

rejection (%)=[1−{(back mutation colony number in sample test section−back mutation colony number in negative control)÷(back mutation colony number in positive control−back mutation colony number in negative control)}]×100

Figures 1, 2:
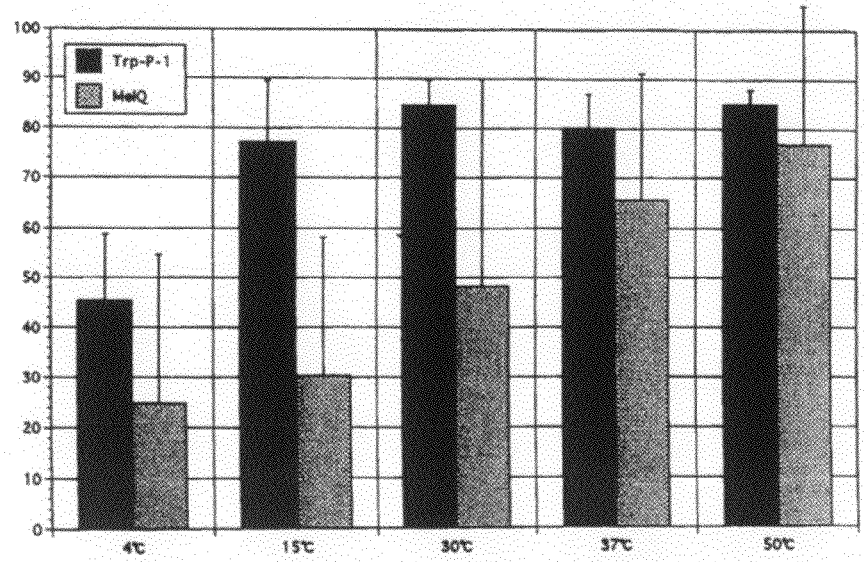
Figures 1, 2:
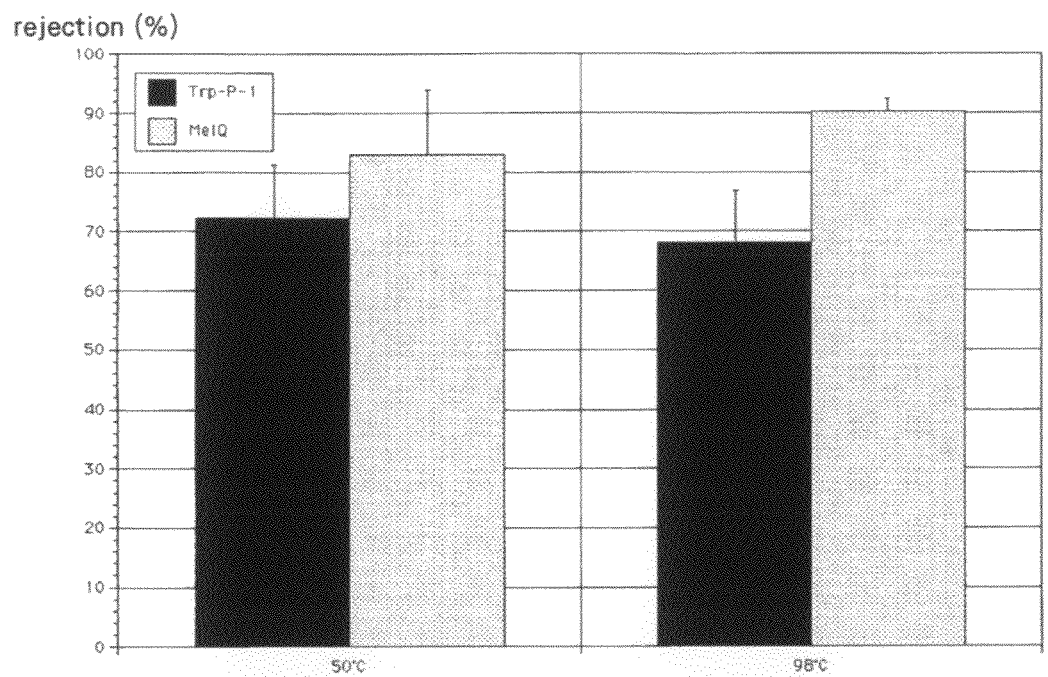
Figure 2:
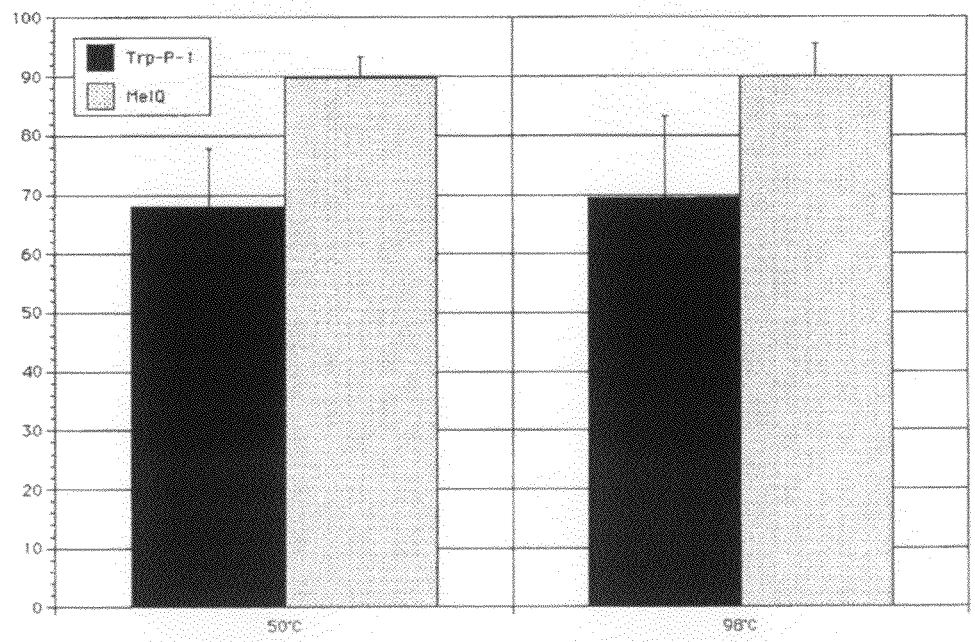

The difference in rejection due to the difference in the temperature at which the PBS (−) suspension liquid of KK-2503 or KN-15 is left still when the above described sample 1 is prepared is explained below. FIGS. 1-1 and 1-2 show the rejection as measured after the PBS (−) suspension liquid of KN-15 and KK-2503 are left still for 24 hours for each temperature. The results show that as the temperature at which the suspension liquid is left still rises, the rejection increases. In addition, the rejection is measured after the two suspension liquids (PBS 0 suspension liquids of KN-15 and KK-2503) are left still for 30 minutes at 50° C. and 98° C. (boiling water) when Sample 1 is prepared, and the results shown in FIGS. 2-1 (KN-15) and 2-2 (KK-2503) are gained.

It is clear from the above results that live bacteria can be left still at a temperature of 50° C. or higher for a short period of time in order to mass produce AMS-LAB in accordance with a method for leaving live bacteria suspended in a medium, and the resulting substance is resistive to heat. It can also be confirmed that live bacteria can be left still over a longer period of time, for example for several months, at 4° C., for example, in order to gain AMS-LAB without fail, and thus, a method for leaving bacteria for a long period of time at a low temperature can also be used as one method for mass production. In addition, high activity can be gained within 30 minutes when the bacteria are left still at 50° C., and in some cases the results are stable when the state is held for approximately 12 hours to 24 hours, and thus, samples that are left still for 12 hours at 50° C. were used in some of the following examples of experiment.

Figures 1, 3:
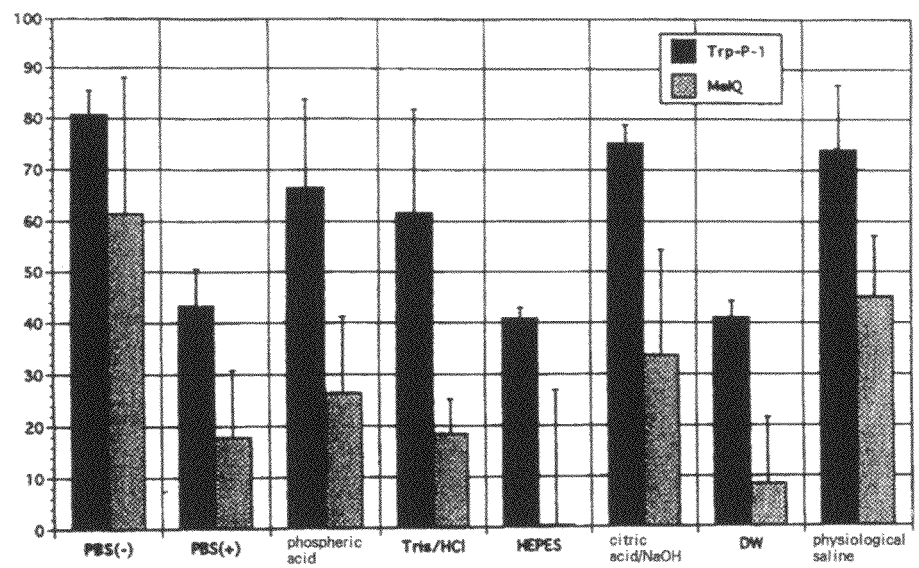
Figures 2, 3:
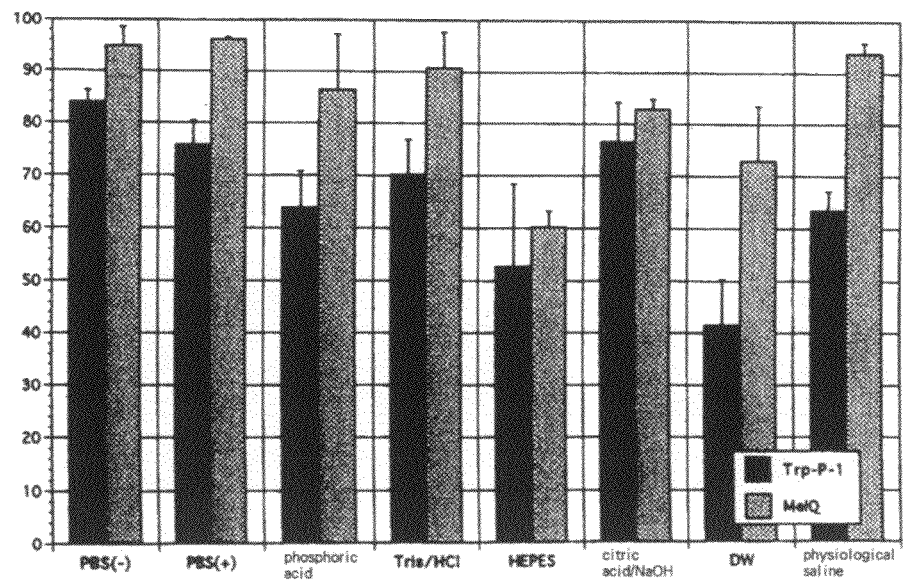

Next, the difference in rejection of the antimutagenicity resulting from the difference in the suspension medium used for the live bacteria suspending liquids for KK-2503 and KN-15 when Sample 1 is prepared is explained. As shown in FIGS. 3-1 (difference in rejection of antimutagenicity resulting from difference of KN-15 suspension medium) and 3-2 (difference in rejection of antimutagenicity resulting from difference of KK-2503 suspension medium), eight suspension media (PBS (−), PBS (+), a phosphate buffered liquid, a Tris (product number T-1503, made by SIGMA Corporation)/HCL buffered liquid, HEPES (product number H-3375, made by SIGMA Corporation), a citric acid/NaOH buffered liquid, distilled water (DW) and physiological saline) are prepared (10 mM was prepared for each, except for the distilled water and physiological saline), and live bacteria are suspended in the respective media and left suspended for 12 hours at 50° C., and the activity was strongest and the yield highest when the bacteria were suspended in PBS (−) of 10 mM with a pH of 7.0 to 7.4.

Here, the composition of the suspension media used is as follows.

In addition, the media used in the examples according to the present invention have the following compositions. It is preferable to sterilize these media in accordance with a high pressure heating method or a filtering method after preparation and before use.

Here, all the salts are commercially available special grade products made by Wako Pure Chemical Industries, Ltd., unless otherwise stated.

PBS (−)
NaCl: 8.0 g
KCl: 0.2 g
$Na_2HPO_1$: 1.15 g
$KH_2PO_4$: 0.2 g
These were dissolved in 1000 ml of distilled water.

PBS (+)
NaCl: 8.0 g
KCl: 0.2 g
$Na_2HPO_4$: 1.15 g
$KH_2PO_4$: 0.2 g
These were dissolved in 800 ml of distilled water (A).
$CaCl_2$: 0.5 g
This was dissolved in 500 ml of distilled water (B).
$MgCl_2.6H_2O$: 0.5 g
This was dissolved in 500 ml of distilled water (C).
These were separately sterilized and mixed in a ratio of A:B:C=8:1:1 (volume ratio).

Phosphate Buffered Liquid 40.5 ml of 0.2 M $Na_2HPO_4$ and 9.5 ml of 0.2 M $NaH_2PO_4$ were mixed and diluted with distilled water so that the final concentration was 10 mM (pH: 7.4).

Tris/HCl Buffered Liquid

Trizma base, with the product number T-1503 made by SIGMA Corporation, was dissolved in distilled water and the pH was adjusted to 7.2 to 7.4 with hydrochloric acid, and after that, distilled water was added so that the concentration was 10 mM.

HEPES Buffered Liquid

HEPES, with the product number H-3375 made by SIGMA Corporation, was dissolved in distilled water so that the concentration was 10 mM.

Citric Acid/NaOH Buffered Liquid

Citric acid anhydride was dissolved in distilled water and the pH was adjusted to 7.2 to 7.4 with a sodium hydroxide solution, and after that, distilled water was added so that the concentration was 10 mM.

Physiological Saline

Sodium chloride was dissolved in distilled water so that the concentration was 0.85% (W/V).

Figures 1, 4:
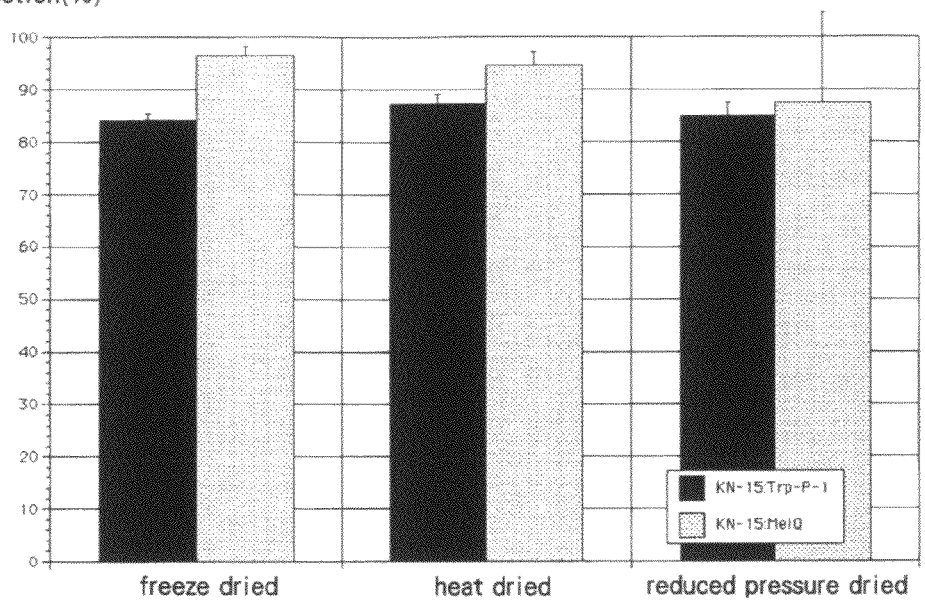
Figures 2, 4:
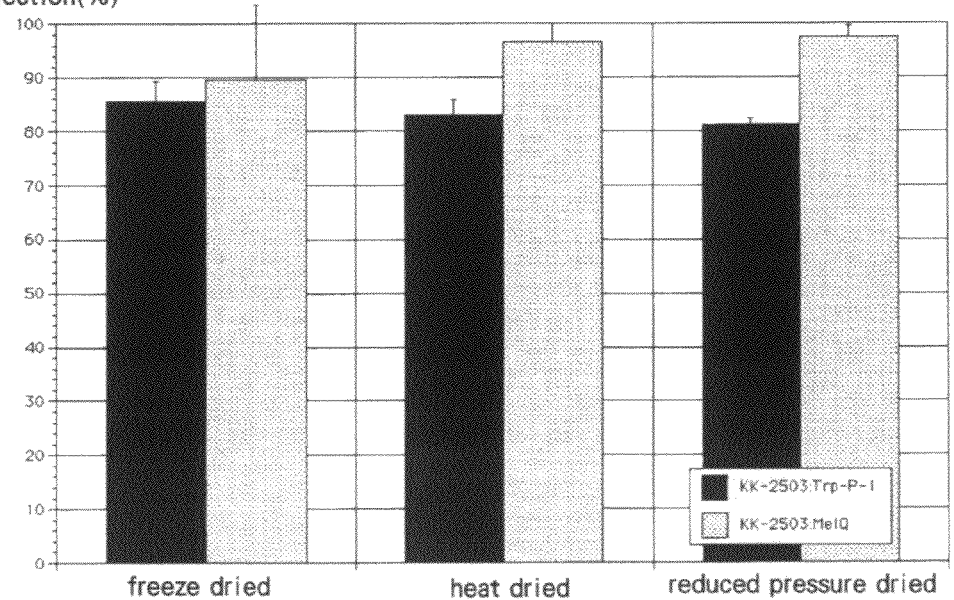

Next, the results of different drying methods when the above described Sample 2 was prepared are shown. The bacterial cells of KN-15 and KK-2503 washed as described above were dried in accordance with each of a freeze drying, heat drying and reduced pressure drying method. The bacterial cells were cultivated in an MRS liquid culture medium, and after that, divided into three equal amounts with each being washed twice with distilled water, and only bacterial cells were collected through centrifugal separation and dried in the following drying method. In the freeze drying, the bacterial cells were frozen at −80° C., and after that, dried for 18 hours using a freeze dryer (FREEZE DRYER FD-5N) made by Tokyo Rikakikai Co., Ltd. In the heat drying, a heat dryer (Drying Sterilizer SH400) made by Yamato Scientific Co., Ltd. was used, and the bacterial cells were dried for one hour at 105° C. In the reduced pressure drying method, a reduced pressure dryer (VACUUM OVEN AVO-310) made by AS ONE Corporation was used, and the bacterial cells were dried for two hours at 70° C. These were suspended in PBS (−) so that the concentration was the same as in the above described MRS liquid culture medium, and they were stirred for 30 seconds at a rotation of 2500 using the TUBE MIXER TRIO TM-1 made by AS ONE Corporation. After that, the mixtures were centrifugally separated for 10 minutes at 10,000 G and the supernatant was adopted and filtered with a 0.2 μm in filter, and was then subjected to an Ames test (FIG. 4-1 shows the results for KN-15 and FIG. 4-2 shows the results for KK-2503). It can be understood from the results that AMS-LAB was generated in the suspension liquid at the moment when bacterial cells were suspended in PBS (−) after being dried.

Figures 1, 5:
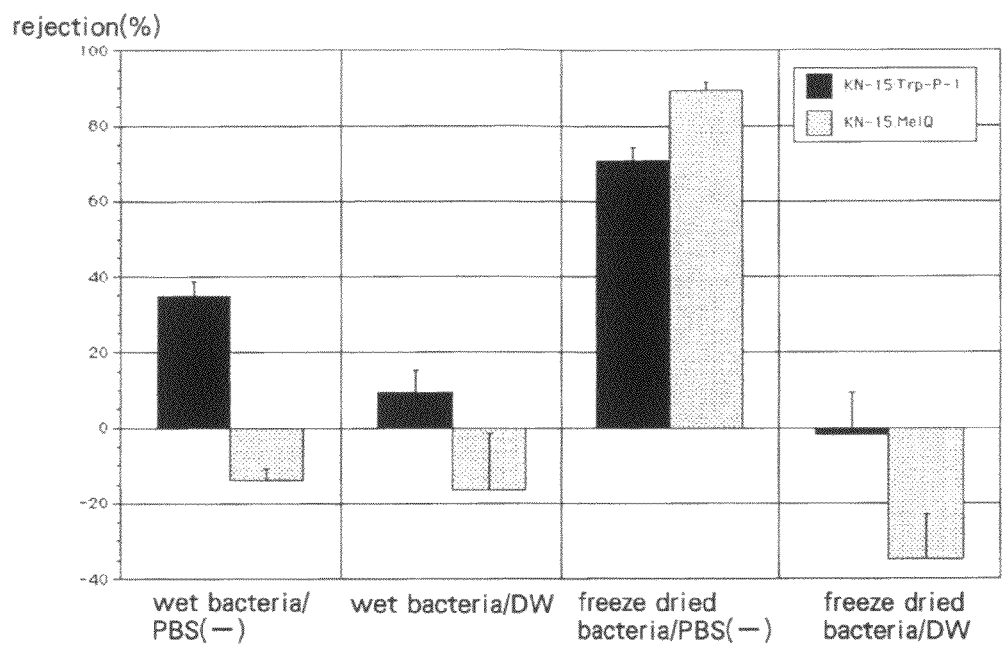
Figures 2, 5:
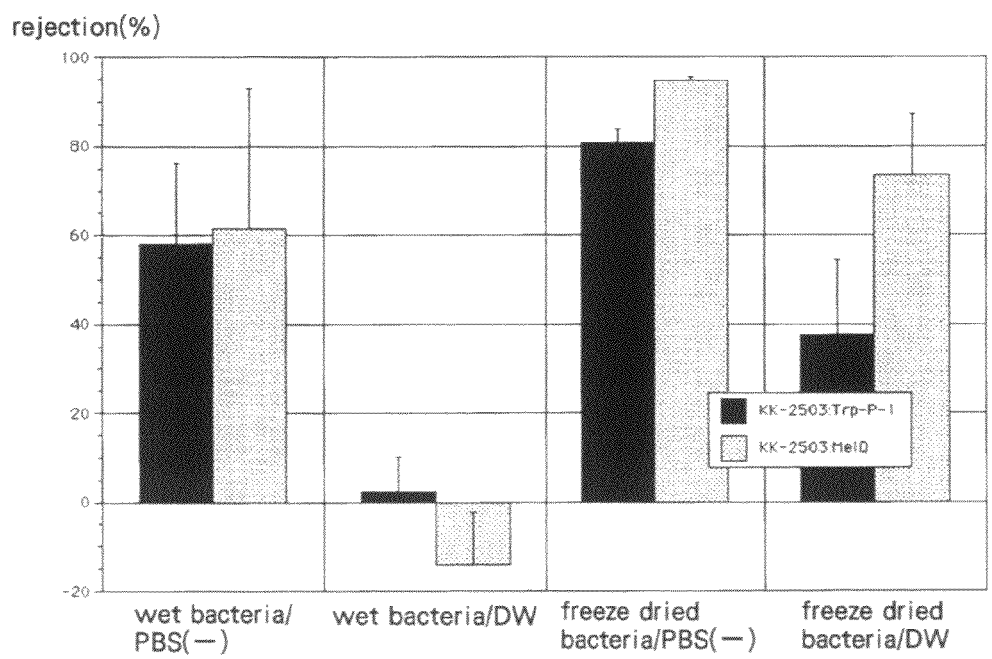

Next, the above described freeze dried bacterial cells of KN-15 and KK-2503 and wet bacterial cells (bacterial cells before the drying process, such as the freeze drying process) were compared. The two were cultured in the above described MRS liquid culture medium and divided into two equal amounts so that freeze dried bacterial cells and wet cells which had not been dried were provided. These were suspended in PBS (−) or distilled water in the same manner as the above and stirred for 30 seconds at a rotation of 2500, and the supernatant was subjected to an Ames test (FIG. 5-1 shows the results for KN-15 and FIG. 5-2 shows the results for KK-2503). It can be understood from the results that the supernatant of the stirred suspension of both strains of dry bacterial cells exhibited a high level of activity while the level of activity of wet bacteria remained low. Meanwhile, it can be seen that even the wet bacteria of the KK-2503 strain instantly exhibited a medium level of activity when suspended in PBS (−) and the freeze dried bacterial cells of the KK-2503 strain exhibited a high level of activity even when suspended in distilled water.

Figures 1, 6:
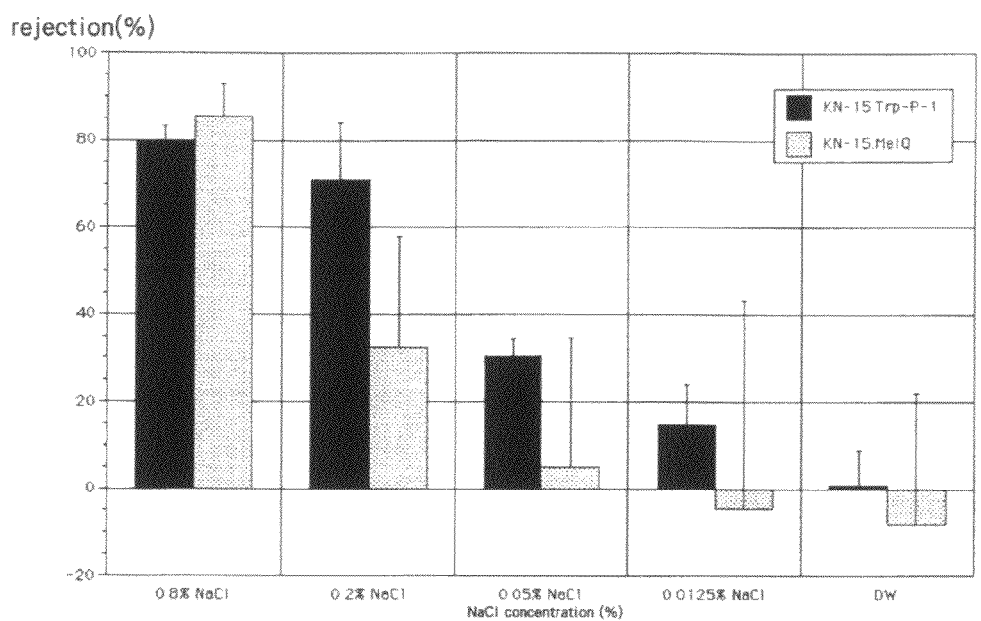
Figures 2, 6:
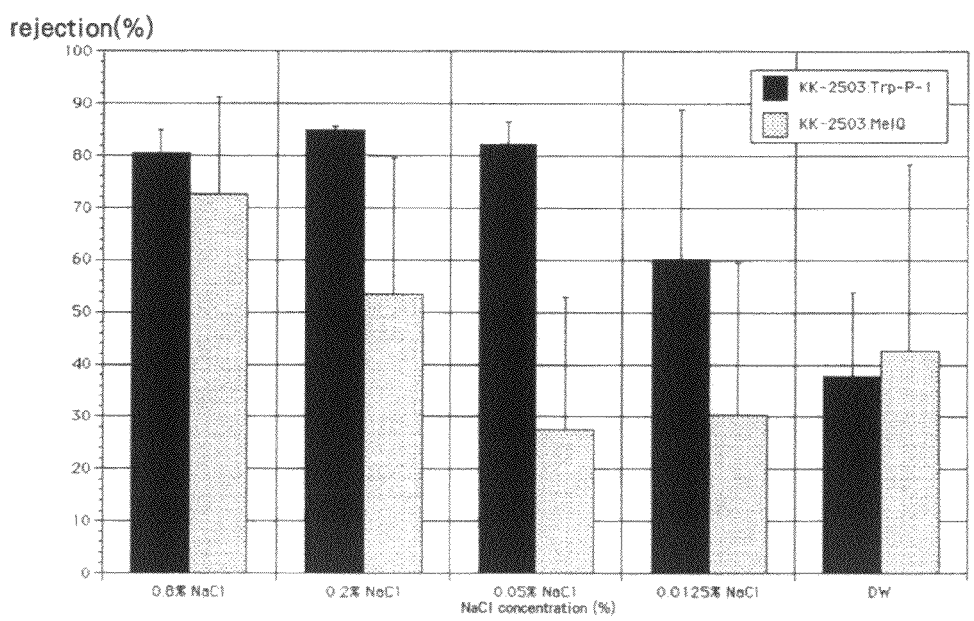

Next, the above described washed bacterial cells of KN-15 and KK-2503 were freeze dried and then suspended in salt water of various concentrations and stirred in the same manner as in the above, and thus, the rejection of the supernatant was measured (FIG. 6-1 shows the results for KN-15 and FIG. 6-2 shows the results for KK-2503). It can be understood from the results that AMS-LAB was generated in accordance with the salt concentration when a salt solution was used instead of PBS (−). In addition, it can be understood that the activity could be instantly gained even when suspended in a solution without salt, for example, distilled water, after being once dried in the case of KK-2503.

Next, general properties of the AMS-LAB gained from the above described two types of lactic acid bacterial strains (KK-2503 and KN-15) are described.

The above described two types of lactic acid bacterial strains (KK-2503 and KN-15) were cultured in 10 ml of an MRS liquid culture medium for 24 hours at 30° C., and after that, suspended in 1/1 of the sterilized PBS (−). These were left still for 12 hours at 50° C., and after that, bacterial cells were removed through centrifugal separation and filtered through a filter of 0.2 μm. The thus gained supernatant (AMS-LAB/PBS (−)) was used on the same day so that the following one sequence of experiments was carried out on the above described Trp-P-1 and MeIQ using an Ames test.

The antimutagenic effects of the AMS-LAB/PBS (−) in an Ames test are not due to direct toxicity against the above described *Salmonella typhimurium* TA98 bacteria, and the mutagenicity of the AMS-LAB itself was not observed at least as long as the test was carried out using samples prepared under the above described conditions.

Next, pepsin was added to a solution where 1N HCl was added to the AMS-LAB/PBS (−) and the pH was adjusted to approximately 2.5 so that the concentration was 0.32%, and after that, a digesting reaction was induced for 90 minutes at 37° C. with a vibration of 120 times per minute. Furthermore, 1N NaOH was added so that the pH was returned to approximately 7.0 and pancreatin was added so that the concentration was 0.1%, and subsequently, a digesting reaction was induced under the same conditions. Next, the solution was boiled for 20 minutes (98° C.) so that the activity of the digestive enzyme was lost (digestive liquid process in FIGS. 7-1 and 7-2). The AMS-LAB/PBS (−), to which the above described digestive enzymes (pancreatin and pepsin) and the above described pH adjustors (HCl and NaOH) were not added (unprocessed control in FIGS. 7-1 and 7-2), and the PBS (−), to which the above described digestive enzymes (pancreatin and pepsin) and the above described pH adjustors (HCl and NaOH) were added so that the concentration became the same as above (digestive liquid control in FIGS. 7-1 and 7-2), were prepared as controls and processed under the same conditions.

Figures 1, 7:
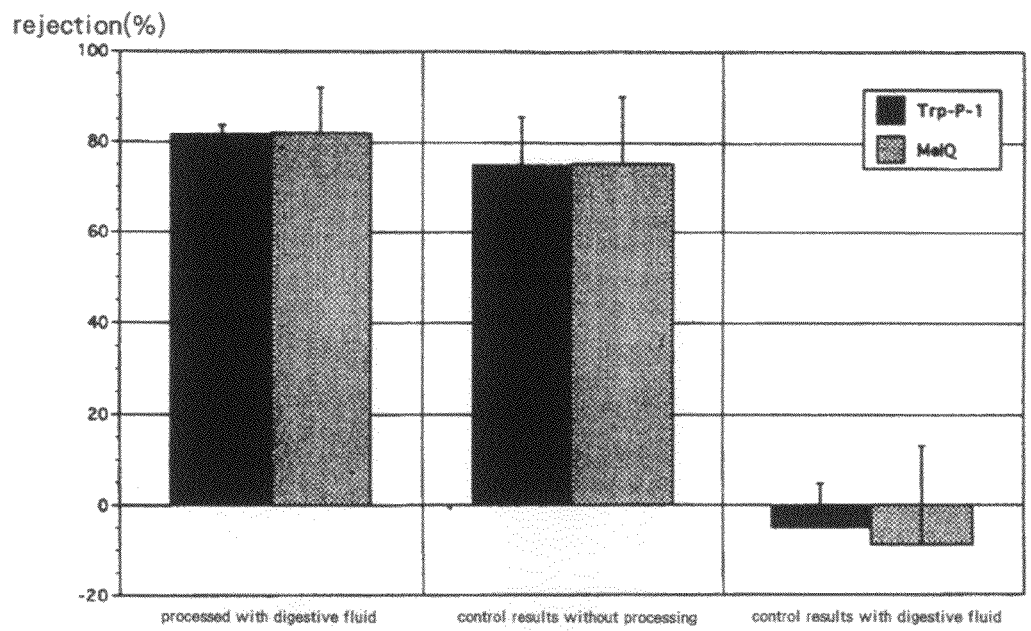
Figures 2, 7:
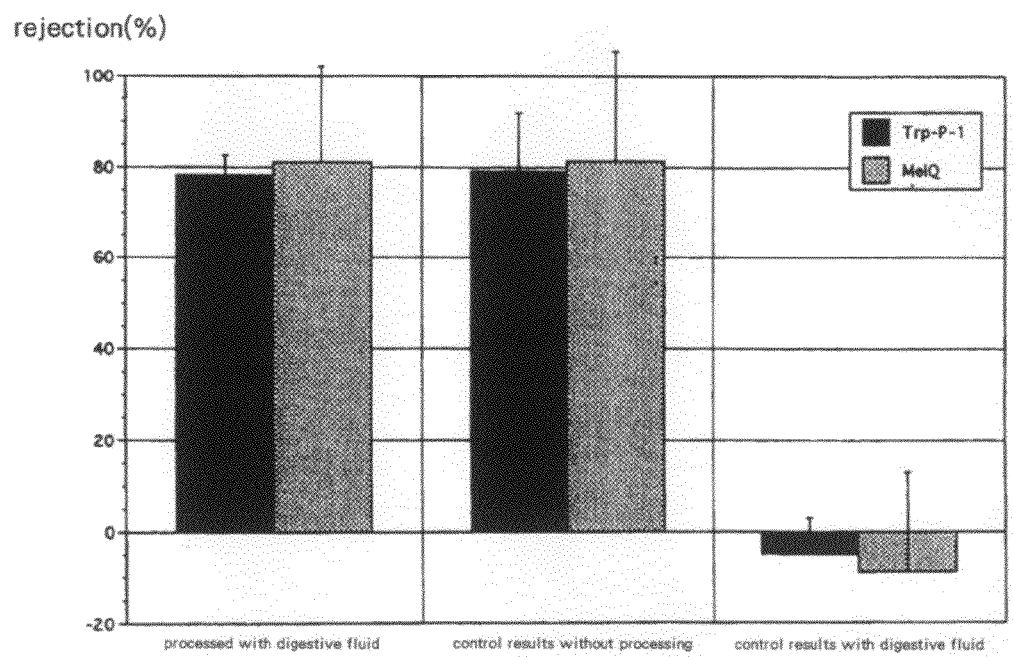

The antimutagenic activities of these were checked to find that almost no activity was lost when the ANS-LAB/PBS (−) was processed with a digestive enzyme (FIGS. 7-1 and 7-2).

Here, the respective tests were carried out at least three times, and the average values of the three results are shown together with standard deviation values in the test results shown in the above.

In addition, the above is the results of tests in vitro, and the results of tests in vivo using mice are described in the following.

Freeze dried AMS-LAB/PBS (−) of KN-15 and freeze dried AMS-LAB/DW (AMS-LAB gained from the supernatant of the suspension where KN-15 is suspended in sterilized diluted water) were prepared, and these were administered to mice orally so that the damage to the cell nuclei by carcinogenic substances was checked using alkaline single-cell gel electrophoresis, which is commonly known as comet assay.

The damage to the cell nuclei by carcinogenic substances is a phenomenon that can trigger cancer later, and the comet assay was carried out basically in accordance with the method by Sasaki et al. (Sasaki Y. F. et al., Detection of rodent liver carcinogen genotoxicity by the alkaline single-cell gel electrophoresis (Comment) assay in multiple mouse organs (liver, lung, spleen, kidney and bone marrow). Mutation Res. 1997, 391. 201-214). The details are described in the following.

SAMPLES

KN-15 preserved at -80° C. was unfrozen and 20 µl was inoculated in 10 ml of an MRS liquid culture medium, which was then cultured for 24 hours at 30° C. This was once transplanted, and 24 hours later, 4 ml was inoculated in 2 liters of an MRS liquid culture medium, which was then cultured for 48 hours at 30° C. This was centrifugally separated for 20 minutes under 1500 G at 4° F., and washed twice with cooled sterilized distilled water or cooled sterilized PBS 0, and after that, condensed and suspended in 500 ml of sterilized distilled water or sterilized PBS (−). This was left still at 37° C. for 48 hours in the case when suspended in distilled water (AMS-LAB/DW) and for one week in the case when suspended in PBS (−) (AMS-LAB/PBS (−)). After that, this was centrifugally separated under the above described conditions so that the supernatant was adopted and filtered with a filter of 0.2 µm, and after that, dried using the above described freeze dryer so that freeze dried products of AMS-LAB/PBS 0 and AMS-LAB/DW were gained in 24 hours.

Reagent 1,2-dimethylhydrazine (DMH made by Tokyo-Kasei Industries Co., Ltd.) was used as a carcinogenic substance.

Composition of Buffered Liquid for Homogenization 75 mM NaCl
24 mM Na/EDTA
pH: 7.5

Composition of Liquid where Cells are Dissolved

NaCl: 14.61 g
EDTA dihydrate: 3.7224 g
Tris: 0.12114 g
DMSO: 10 ml
Triton-X: 1 ml These were dissolved in distilled water so that the volume was 100 ml (pH: 10.0).

Composition of EP Buffered Liquid

NaOH: 12 g
EDTA: 0.292 g

These were dissolved in distilled water so that the volume was 1000 ml and the pH was adjusted to 13.0.

Low Temperature Dissolved Agarose Solution

Agarose L (made by Wako Pure Chemical Industries, Ltd.) was dissolved in PBS (−) so that the concentration was 0.5° A, which was divided and preserved at room temperature. This was converted to sol by means of an electric oven and preserved at 37 immediately before use.

Slide Glass

A 0.75% agarose solution (Agarose 1500 made by Dojindo Laboratories) was prepared and preserved in a beaker on a hot plate at approximately 80° C. At the same time, a beaker with distilled water in it was also placed on a hot plate at the same temperature, and a piece of slide glass was put in it.

The slide glass was taken out from the distilled water at 80° C. and immediately put into the beaker with the agarose solution so that the surface of the slide was sufficiently submerged and immediately taken out. After the extra solution was well shaken off, the agarose solution was wiped off from one surface with a paper towel. The slide glass was placed so that the surface on which the agarose solution remained faced upwards and left to dry naturally, and thus, a thin agarose film was prepared on the slide glass.

A number of pieces of slide glass as described above were prepared in advance for use.

Propidium Iodide Solution

Propidium iodide (made by Wako Pure Chemical Industries, Ltd.) was dissolved in distilled water at a ratio of 1 mg/ml and then divided and preserved at -28° C. This was unfrozen and distilled to 20 times thinner with PBS (−) immediately before use.

Test Animals

CD-1 mice (7-weeks old males) were purchased from Charles River Laboratories Japan Inc., placed in sterilized cages for mice so that each cage contained four mice, and then raised in a vivarium. As for the conditions for breeding, the room temperature was maintained at 23° C.+/−2° C., the humidity was maintained at 50%+/−10%, and the darkness and brightness were switched at 12 hour intervals in the vivarium. One week after purchase, the mice were observed to see if there were any abnormalities, and after that, they were subjected to experiments at the point in time when they reached 8 weeks old. During breeding, they fed freely on pellets of MF (product name) purchased from Oriental Yeast Co., Ltd., and they could also drink faucet water freely.

EXPERIMENT 1

The above described freeze dried product of ANIS-LAB/PBS 0 was mixed with powder MF so that the product became 1 mass %, and thus, dried products in biscuit form were prepared. As controls, products in biscuit form made only of MF powder and products in biscuit form made by mixing salts having the above described PBS (−) composition the same amount of in with the powder MF as in the freeze dried product of AMS-LAB/PBS (−) were prepared.

The above described biscuits were left out for groups of four mice. One week later DMH (dimethyl hydrogen) dissolved in approximately 0.5 ml of PBS (−) with a ratio of 20 mg per kilogram of the body weight of the mice was orally administered into the mice using a stomach sonde.

EXPERIMENT 2

The above described freeze dried products of AMS-LAB/ DW were dissolved in PBS 0, and 50 mg/0.5 ml per mouse was orally administered into mice using a stomach sonde. 30 minutes later 30 mg per kilogram of the body weight of the mice of DMH dissolved in approximately 0.5 ml of PBS (−) was administered into the mice in the same manner. This was done in the same manner as in the above experiment 1, except that only DMH was administered in positive control groups and only PBS (−) was administered in negative control groups.

Comet Assay

Three hours after administering the DNH, the mice were anaesthetized using diethyl ether (Wako Pure Chemical Industries, Ltd.) and decapitated, and the liver and colon were collected. The inside of the colons was washed with PBS (−), and immediately after that the colons were cut open in their length, and the mucous membrane was collected using a scraper.

After the measuring their weight, the livers were put in a potter type homogenizing container filled with 10 ml of an ice cold homogenizing buffer liquid as they were, and homogenized at an ice cold temperature and rotated 800 times per minute until uniform.

Likewise, the mucus membranes were put in a potter type homogenizing container filled with 5 ml of an ice cold homogenizing buffer liquid and homogenized under the same conditions.

After the completion of homogenizing, the homogenate was centrifugally separated for 10 minutes under 700 G. The homogenate of the liver was washed three times with PBS (−). The mucous membranes were used without being washed.

After the completion of centrifugal separation, the homogenate was floated in a low temperature melted agarose solution kept at 37° C., so that the number of cell nuclei became approximately $10^6$/ml. One slide was divided into two sections, and 75 μl of the liquid with the same floating sample was put in each section and covered with a glass cover (duplicate). One slide for liver samples and one slide for mucous membranes were prepared per mouse.

These were put in a stainless steel vat and covered with an aluminum foil so as to block light, and kept at. 4° C. for 10 minutes so that the agarose solidified. After solidification, the glass covers were carefully removed and the vat filled with a cell dissolving liquid until the surface of the slides was completely immersed, and this was again kept at 4° C. with light blocked.

One hour later the cell dissolving liquid was discarded and the slides installed in submarine type electrophoretic apparatuses (AE-6111 submerge agarose electrophoresis apparatus made by ATTO Corporation) filled with an EP buffer liquid.

The used EP buffer liquid was cooled to 4° C.; in advance, and each electrophoretic apparatus was shielded from light and cooled with ice while used. The slides were kept in the EP buffer liquid for 40 minutes, and after that, electrophoresis was carried out at 25 V and 300 mA for 20 minutes. After the completion of electrophoresis, the slides were washed three times with a 0.4 M Tris/HCL buffer liquid (having a pH of 7.5) and fixed with methanol, and then dried with wind.

After that, a propidium iodide solution was added in the container in which the slides were put, and the slides were dyed for 10 minutes while being vibrated slowly on top of a shaking table, and then rinsed with distilled water and dried with wind, so that sample slides were gained.

These were observed through a fluorescent microscope (DMLB2, made by LEICA Microsystems GmbH) in a dark room, and after that, images were taken using a CCD camera (DC480, made by LEICA Microsystems GmbH) and stored in a computer. The images of the slides were taken with a magnification of 100, and the wavelength for exciting the fluorescent light was 546 nm and the absorption wavelength 590 nm. The stored images were analyzed using the personal computer, using image analyzing software Lab Works 4.0 (made by UVP Corporation), and thus, the length of the cell nuclei was measured.

50 cell nuclei per section of slide were measured, and the average value for the two sections was taken as the value for one mouse. As for the length of the cell nuclei, the value gained by subtracting the diameter of the nuclei from the entire length was taken as the migration length in micrometers. The results were examined in accordance with the Tukey's HSD method after being processed for dispersion analysis (ANOVA). It could be determined that there is a significant difference when $p<0.05$.

Figures 1, 8:
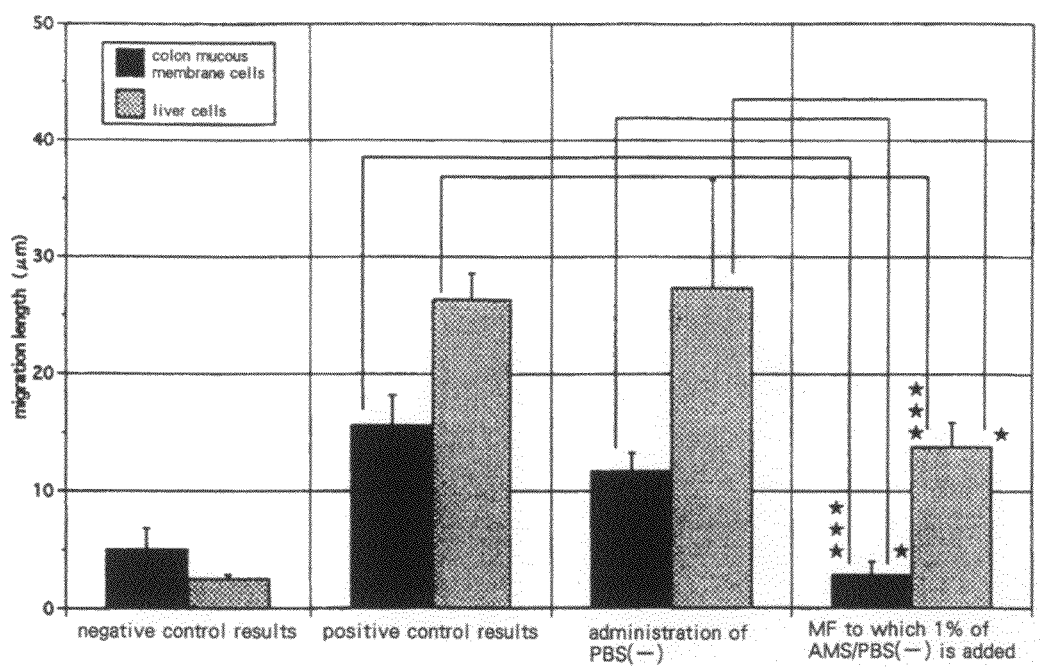
Figures 2, 8:
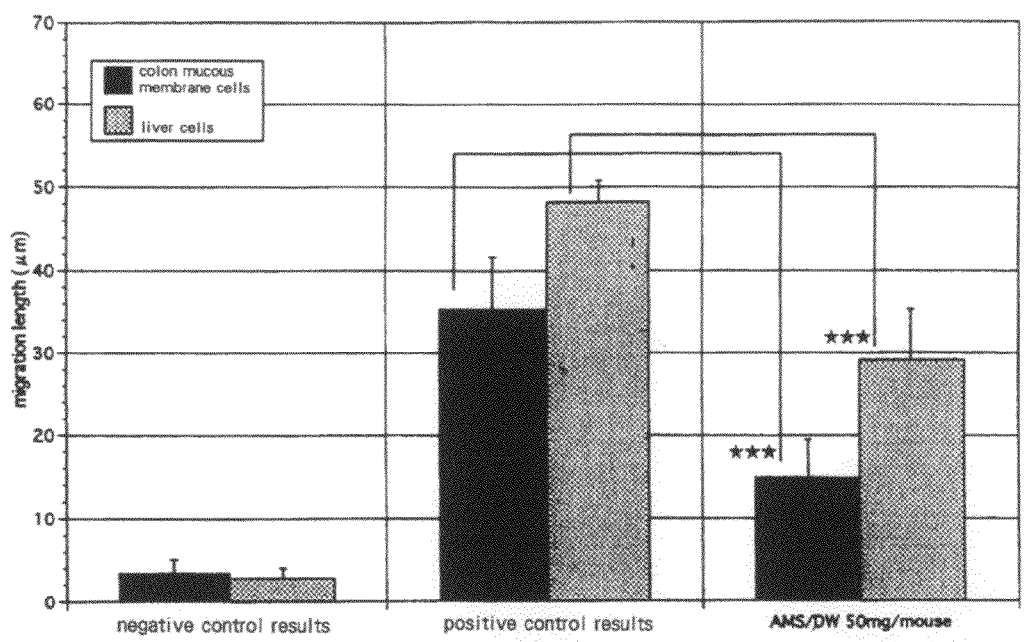

The results are shown in FIG. 8-1 (Experiment 1: Effects of defense of MF with 1% of freeze dried AMS-LAB/PBS (−) of KN-15 against colon mucus membrane cell and liver cell nuclei disorder induced by administering 20 mg/kg of DMH into CD-1 mice (eight-weeks-old males, n=4) through their food for one week: migration length (μm): ★ $p<0.05$, ★★★ $p<0.001$) and FIG. 8-2 (Experiment 2: Effects of defense of 50 mg/mouse of freeze dried AMS-LAB/DW of KN-15 against colon mucus membrane cell and liver cell nuclei disorder induced by administering 30 mg/kg of DMH into CD-1 mice (eight-weeks-old males, n=4) a single time migration length (μm): ★★★ $p<0.001$).

It became clear from the results of the comet assay that AMS-LAB is not only effective in experiments in vitro but also have antimutagenic properties in vivo when ingested orally, and furthermore, is effective against other carcinogenic substances, such as dimethyl hydrogen, in addition to HCA.

Though the above experiments were all carried out using *Lactobacillus plantarum* KK-2503 (KK-2503) and *Lactobacillus alimentarius* KN-15 (KN-15), the following shows that AMS-LAB can be gained from many types of lactic acid bacteria.

Figures 1, 9:
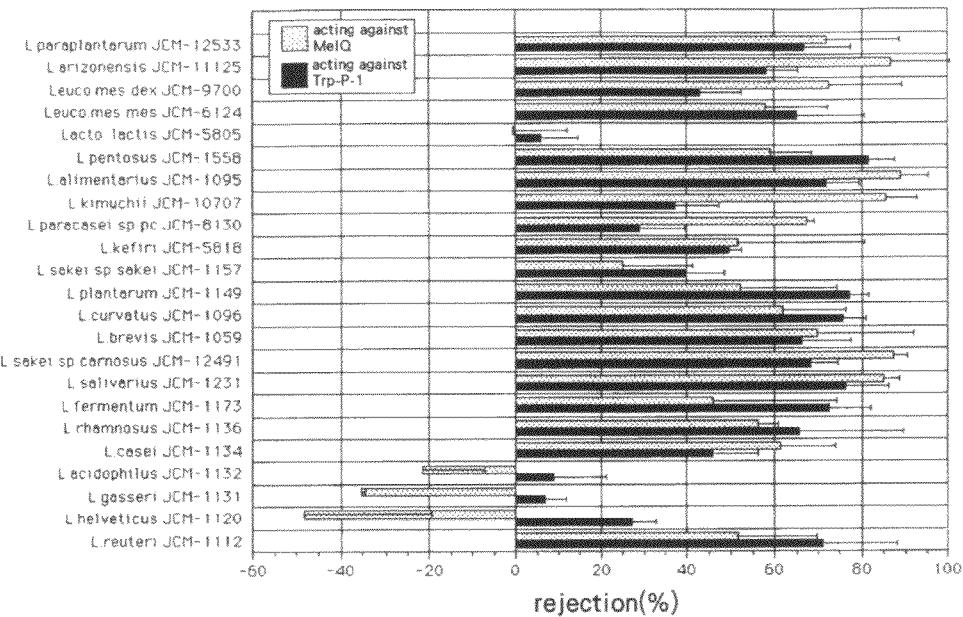
Figures 2, 9:
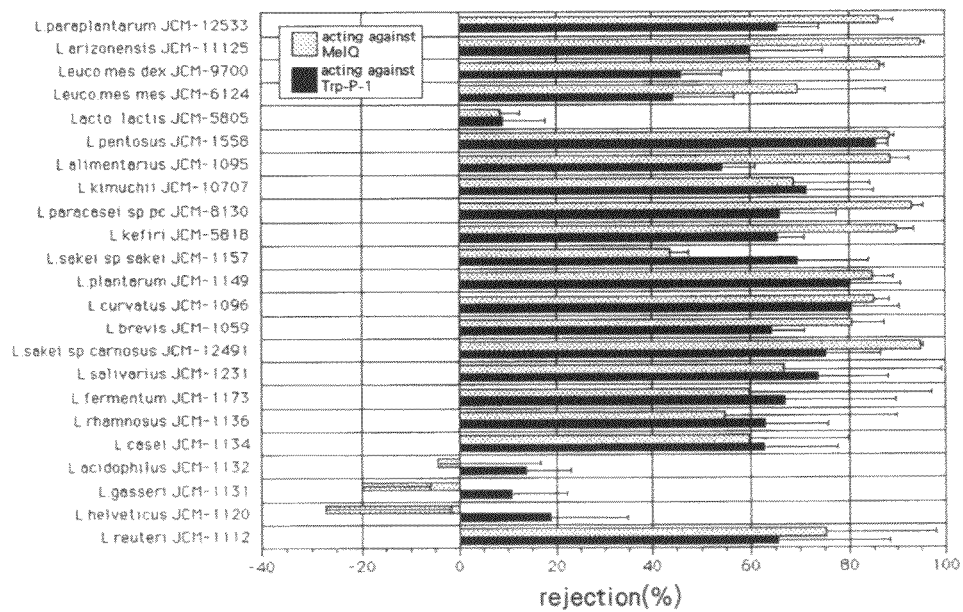
Figure 10:
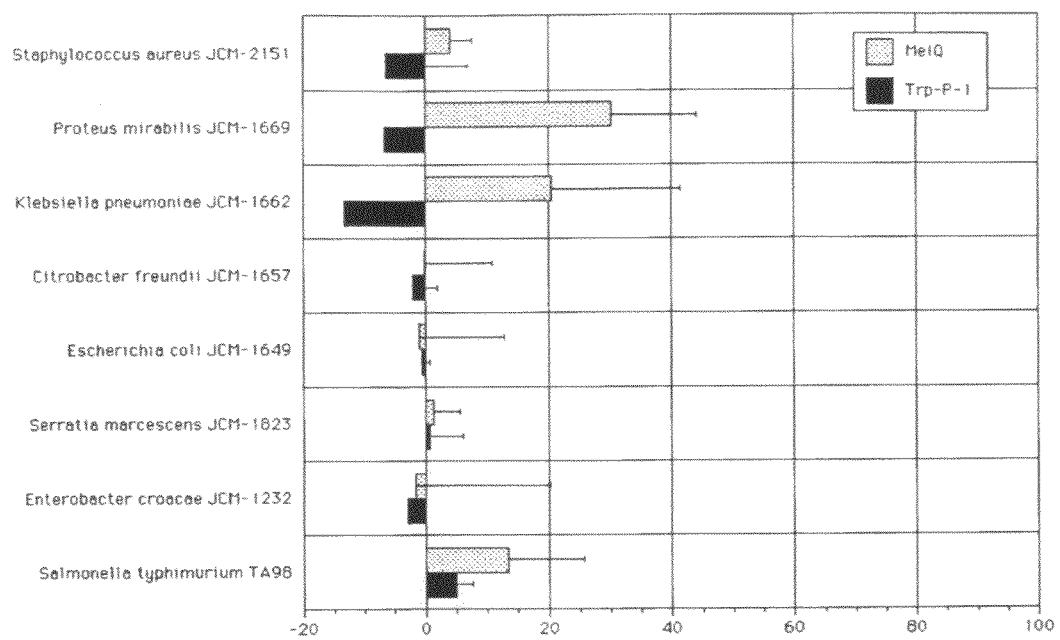
FIG. 10 is a graph showing the relationship between standard strains of intestinal Grain negative bacteria, such as colon *bacillus*, or pathogenic Grain positive bacteria, such as yellow *staphylococcus*, and the antimutagenic activity against HCA. Samples gained by freeze drying live bacteria and after that suspending and stirring them in 0.8 mass % saline were used.

Standard strains of 23 types of lactic acid bacteria (purchased from the independent administrative institution Riken BioResource Center) were used, and live bacteria of these were cultured in 10 ml of an MRS liquid culture medium for 24 hours at 30° C.; or 37° C., and after that, the bacterial cells were centrifugally washed with distilled water and collected, and then suspended in 10 ml of PBS (−), which was left still for 30 minutes at 50° C. so that AMS-LAB was mass produced as a sample (corresponding to the method for preparing the above described Sample 1). Alternatively, the live bacteria could have been washed, and after that freeze dried and suspended in 10 ml of 0.8% saline in order to mass produce AMS-LAB as a sample (corresponding to the method for preparing the above described Sample 2). As a result of an Ames test on these samples, it was confirmed that many of the standard strains had AMS-LAB activity (FIG. 9-1 shows the results in the case where wet bacteria were left still for 30 minutes at 50° C., and FIG. 9-2 shows the results for freeze dried bacterial cells). Meanwhile, Gram negative bacteria, such as colon *bacillus*, which was used as a control, and yellow *Staphylococcus*, which causes food poisoning, did not have any activity at all (FIG. 10). These bacteria were cultured in 30 ml of an NB liquid culture medium with 0.5 mass % NaCl (Difco) for 24 hours at 37° C. with a vibration of 120 time/min and washed with distilled water (DW) and after that freeze dried and suspended in 1/1 of 0.8% saline, as in the case of strains of lactic acid bacteria, and then the supernatant was used as a sample. FIG. 10 shows the results of the Ames test on this sample.

That is to say, it can be said that though the amount of mass produced AMS-LAB and the degree of the antimutagenic activity of AMS-LAB are different depending on the bacteria species, the type of bacteria and the strain, many types of lactic acid bacteria hold or produce AMS-LAB, while most other bacteria, referred to as "pathogenic bacteria," do not. In other words, it is clear that whether or not. AMS-LAB is produced is one very important factor sharply distinguishing so-called "probiotic bacteria" from "pathogenic bacteria."

Standard strains of lactic acid bacteria are *Lactobacillus alimentarius* JCM-1095, *Lactobacillus plantarum* JCM-1149, *Lactobacillus fermentum* JCM-1193, *Lactobacillus pentosus* JCM-1558, *Lactobacillus arizonensis* JCM-11125, *Lactobacillus paraplantarum* JCM-12533, *Lactobacillus brevis* JCM-1059, *Lactobacillus curvatus* JCM-1096, *Lactobacillus reuteri* JCM-1112, *Lactobacillus herbeticus* JCM-1120, *Lactobacillus gasseri* JCM-1131, *Lactobacillus acidophilus* JCM-1132, *Lactobacillus casei* JCM-1134, *Lactobacillus rhamnosus* JCM-1136, *Lactobacillus sakei* JCM-1157. *Lactobacillus salivarius* JCM-1231, *Lactobacillus sakei* subspecies *carnosus* JC1V1-12491, *Lactobacillus kefiri* JCM-5818, *Lactobacillus paracasei* JCM-8130, *Lactobacillus kimchi* JCM-10707. *Leuconostoc mesenteroides* JCM-9700 and *Lactococcus lactis* JCM-5805.

Next, the method for collecting AMS-LAB gained in the supernatant of the suspension is described. In the case where only AMS-LAB is extracted after suspension in a salt solution, such as PBS (−), for example, the salt is removed. There are various publicly known means for removing salt, such as ultrafilter membrane methods and gel filtering methods, or use of an ODS column, and any of these may be appropriate for use. In the case where there is a possibility of AMS-LAB being lost, for example through adsorption to the filtrating membrane, any appropriate method can be modified for filtration.

In addition, it was confirmed that AMS-LAB can be adopted in accordance with a method for adsorbing AMS-LAB after an ODS column is equilibrated with 70% ethanol, and after that eluting it in a solution of approximately 50% acetonitrile/distilled water. As a simple means, a method for mass producing AMS-LAB through heating after suspending it in ion exchanged water, distilled water or pure water is appropriate for use.

Industrial Applicability

The AMS-LAB gained in accordance with the method according to the present invention can be used after bacterial cells are removed through centrifugal separation or without removing bacterial cells, so that effects of adsorbing antimutagenic substances and immunostimulating effects of the bacterial cells can be expected.

After that, water may be removed so that only the AMS-LAB is extracted, or the AMS-LAB and the bacterial cells may be solidified or powdered.

In addition, the gained AMS-LAB may be used after being sterilized through instant high-temperature sterilization, boiling or high-pressure sterilization, or as it is.

In addition, the AMS-LAB makes it possible for live lactic acid bacterial cells to be suspended in any medium, as long as it is safe for ingestion by humans, for example distilled water, ion exchanged water, pure water, salt water, various types of buffered liquids, so-called isotonic drinks, such as sports drinks, and vitamin-added solutions, so that they can be used for preventing cancer or for health purposes.

Accordingly, it becomes possible to use the AMS-LAB for food products by adding various types of sweeteners and aromas, as well as to develop health foods and medical products having antimutagenic effects by adding various types of fillers.

The invention claimed is:

1. A method for production of antimutagenic substance using lactic acid bacteria, comprising the step of suspending a strain of lactic acid bacteria selected from *Lactobacillus plantarum* KK-2503 (NPMD Accession number: NITE BP-334) or *Lactobacillus alimentarius* KN-15 (NPMD Accession number: NITE BP-333) in a nutrient-free medium to produce an antimutagenic substance that acts against heterocyclic amines.

2. The method for production of antimutagenic substance according to claim 1, wherein the said medium is selected from the group consisting of lithium salt solution, sodium salt solution, potassium salt solution, magnesium salt solution, and calcium salt solution.

\* \* \* \* \*